US008809047B2

(12) United States Patent
Yao

(10) Patent No.: US 8,809,047 B2
(45) Date of Patent: Aug. 19, 2014

(54) HERPES SIMPLEX VIRUS VACCINES

(75) Inventor: Feng Yao, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/517,232

(22) PCT Filed: Dec. 20, 2010

(86) PCT No.: PCT/US2010/061320
§ 371 (c)(1),
(2), (4) Date: Jun. 19, 2012

(87) PCT Pub. No.: WO2011/079073
PCT Pub. Date: Jun. 30, 2011

(65) Prior Publication Data
US 2012/0263752 A1 Oct. 18, 2012

Related U.S. Application Data

(60) Provisional application No. 61/288,836, filed on Dec. 21, 2009.

(51) Int. Cl.
A61K 39/245 (2006.01)
A61P 31/22 (2006.01)
C12N 7/01 (2006.01)
C12N 15/38 (2006.01)
C12N 15/34 (2006.01)
C12N 15/869 (2006.01)
C07K 14/03 (2006.01)
C07K 14/035 (2006.01)
A61K 39/00 (2006.01)

(52) U.S. Cl.
CPC ....... A61K 39/245 (2013.01); A61K 2039/5256 (2013.01); A61K 2039/5254 (2013.01)
USPC ...... 435/320.1; 435/5; 435/91.32; 435/91.33; 435/91.4; 435/91.41; 435/91.42; 435/471; 435/235.1; 424/184.1; 424/231.1; 424/229.1; 424/199.1

(58) Field of Classification Search
CPC ............ C12N 15/86; C12N 2710/16643; C12N 7/00; C12N 2710/16622; C12N 15/111; C12N 2710/16043; C12N 15/8695; A61K 35/763; A61K 39/245; A61K 38/2086; C07K 14/005; C07K 14/035
USPC ............ 435/91.32, 91.33, 91.4, 91.41, 91.42, 435/471, 5, 320.1; 424/184.1, 229.1, 231.1
See application file for complete search history.

(56) References Cited

U.S. PATENT DOCUMENTS

| 5,464,758 | A | 11/1995 | Gossen |
| 5,589,362 | A | 12/1996 | Bujard |
| 5,763,217 | A * | 6/1998 | Cynader et al. ............... 435/69.1 |
| 5,770,414 | A | 6/1998 | Gage et al. |
| 5,917,122 | A | 6/1999 | Byrne |
| 5,965,440 | A | 10/1999 | Reeves |
| 5,972,650 | A * | 10/1999 | Yao ............................... 435/69.1 |
| 6,027,730 | A | 2/2000 | Francotte et al. |
| 6,183,753 | B1 * | 2/2001 | Cochran et al. ............. 424/199.1 |
| 6,251,640 | B1 * | 6/2001 | Yao ............................... 424/93.2 |
| 6,261,552 | B1 | 7/2001 | De Luca |
| 6,444,871 | B1 * | 9/2002 | Yao ............................... 800/4 |
| 6,635,478 | B1 * | 10/2003 | Hippenmeyer et al. ........ 435/325 |
| 6,846,670 | B2 * | 1/2005 | Schwartz et al. .......... 435/320.1 |
| 8,236,941 | B2 * | 8/2012 | Yao ............................... 536/24.1 |
| 2002/0028484 | A1 * | 3/2002 | Yao ............................... 435/69.1 |
| 2003/0113348 | A1 | 6/2003 | Coffin |
| 2003/0165537 | A1 | 9/2003 | Fehler et al. |
| 2004/0029229 | A1 | 2/2004 | Reeves et al. |
| 2004/0063094 | A1 | 4/2004 | Coffin |
| 2004/0229362 | A1 * | 11/2004 | Epstein et al. ................. 435/457 |
| 2005/0266564 | A1 * | 12/2005 | Yao ............................... 435/456 |
| 2006/0116340 | A1 | 6/2006 | Lewin |
| 2008/0008686 | A1 * | 1/2008 | Yao ............................... 424/93.2 |
| 2010/0015687 | A1 * | 1/2010 | Yao ............................... 435/235.1 |
| 2012/0190106 | A1 * | 7/2012 | Yao ............................... 435/320.1 |

FOREIGN PATENT DOCUMENTS

| CN | 1065997 A | 11/1992 |
| CN | 1503843 A | 6/2004 |
| WO | WO 94/04672 | 3/1994 |
| WO | WO 2011/025717 A2 | 3/2011 |

OTHER PUBLICATIONS

Toka FN, Gierynska M, Suvas S, Schoenberger SP, Rouse BT. Rescue of memory CD8+ T cell reactivity in peptide/TLR9 ligand immunization by codelivery of cytokines or CD40 ligation. Virology. Jan. 5, 2005;331(1):151-8.*
Resnick J, Boyd BA, Haffey ML. DNA binding by the herpes simplex virus type 1 ICP4 protein is necessary for efficient down regulation of the ICP0 promoter. J Virol. Jun. 1989;63(6):2497-503.*
Roberts MS, Boundy A, O'Hare P, Pizzorno MC, Ciufo DM, Hayward GS. Direct correlation between a negative autoregulatory response element at the cap site of the herpes simplex virus type 1 IE175 (alpha 4) promoter and a specific binding site for the IE175 (ICP4) protein. J Virol. Nov. 1988;62(11):4307-20.*
Herrlinger U, Pechan PA, Jacobs AH, Woiciechowski C, Rainov NG, Fraefel C, Paulus W, Reeves SA. HSV-1 infected cell proteins influence tetracycline-regulated transgene expression. J Gene Med. Sep.-Oct. 2000;2(5):379-89.*
Preston CM, Mabbs R, Nicholl MJ. Construction and characterization of herpes simplex virus type 1 mutants with conditional defects in immediate early gene expression. Virology. Mar. 3, 1997;229(1):228-39.*

(Continued)

Primary Examiner — Benjamin P Blumel
Assistant Examiner — Rachel Gill
(74) Attorney, Agent, or Firm — Candace M. Summerford; David S. Resnick; Nixon Peabody LLP

(57) ABSTRACT

The present invention is directed to Herpes simplex-2 viruses that may be used in vaccines to immunize patients against genital herpes.

26 Claims, 6 Drawing Sheets

(56) References Cited

OTHER PUBLICATIONS

Loser K, Mehling A, Apelt J, Ständer S, Andres PG, Reinecker HC, Eing BR, Skryabin BV, Varga G, Schwarz T, Beissert S. Enhanced contact hypersensitivity and antiviral immune responses in vivo by keratinocyte-targeted overexpression of IL-15. Eur J Immunol. Jul. 2004;34(7):2022-31.*

Abu-Raddad, et al., "Genital Herpes Has Played a More Important Role than Any Other Sexually Transmitted Infection in Driving HIV Prevalence in Africa," *PLoS ONE* 3(5)(e2230):1-15 (May 2008).

Ackermann, et al., "Characterization of Herpes Simplex Virus 1 α Proteins, 0, 4, and 27 with Monoclonal Antibodies,"*J. Virol.* 52(1):108-118 (Oct. 1984).

Adelson, et al., "Simultaneous detection of herpes simplex virus types 1 and 2 by real-time PCR and Pyrosequencing,"*J Clin. Virol.* 33:25-34 (2005).

Advani, et al., "Friendly Fire: Redirecting Herpes Simplex Virus-1 for Therapeutic Applications," *Clin. Microbiol. Infect.* 8:551-563 (2002).

Akhrameyeva, et al., "Development of a Glycoprotein D-Expressing Dominant-Negative and Replication-Defective Herpes Simplex Virus 2 (HSV-2) Recombinant Viral Vaccine against HSV-2 Infection in Mice,"*J. Virol.* 85(10):5036-5047 (May 2011).

Anderson, W.F., "Human Gene Therapy," *Nature (London)* 392:25-30 (1998).

Arvin, et al., "Detection of Type-Specific Antibody to Herpes Simplex Virus Type 1 by Radioimmunoassay with Herpes Simples Virus Type 1 Glycoprotein C Purified with Monoclonal Antibody," *Infect. Immun.* 40(1):184-189 (1983).

Augustinova, et al., "The Dominant-Negative Herpes Simplex Virus Type 1 (HSV-1) Recombinant CJ83193 Can Serve as an Effective Vaccine against Wild-Type HSV-1 Infection in Mice," *J. Virol.* 78(11):5756-5765 (Jun. 2004).

Berens, et al., "Gene regulation by tetracyclines: Constraints of resistance regulation in bacteria shape TetR for application in eukaryotes," *Eur. J. Biochem.* 270:3109-3121 (2003).

Bourne, et al., "DNA immunization confers protective immunity on mice challenged intravaginally with herpes simplex virus type 2," *Vaccine* 14(13):1230-1234 (1996).

Brans, et al., "Prevention of Genital Herpes Simplex Virus Type 1 and 2 Disease in Mice Immunized with gD-Expressing Dominant-Negative Recombinant HSV-1,"*J. Invest. Dermatol.* 129:2470-2479 (2009).

Brans, et al., "Immunization with a Dominant-Negative Recombinant HSV Type 1 Protects against HSV-1 Skin Disease in Guinea Pigs," *J. Invest. Dermatol.* 128:2825-2832 (2008).

Bryson, et al., "Risk of Acquisition of Genital Herpes Simplex Virus Type 2 in Sex Partners of Persons with Genital Herpes: A Prospective Couple Study," *J. Infect. Dis.* 167:942-946 (1993).

Cai, et al., "The Herpes Simplex Virus Type 1 Regulatory Protein ICPO Enhances Virus Replication during Acute Infection and Reactivation from Latency," *J. Virol.* 67(12):7501-7512 (Dec. 1993).

Cai, et al., "The Herpes Simplex Virus Type 1 ICPO Plays a Critical Role in the De Novo Synthesis of Infectious Virus following Transfection of Viral DNA," *J. Virol.* 63(11):4579-4589 (Nov. 1989).

Clackson, T., "Regulated Gene Expression Systems," *Gene Therapy* 7:120-125 (2000).

Cohen, J., "Bumps on the Vaccine Road," *Science* 265:1371-1373 (Sep. 1994).

Cohen, et al., "Localization and Synthesis of an Antigenic Determinant of Herpes Simplex Virus Glycoprotein D That Stimulates the Production of Neutralizing Antibody," *J. Virol.* 49(1):102-108 (Jan. 1984).

Coleman, et al., "Determination of Herpes Simplex Virus Type-Specific Antibodies by Enzyme-Linked Immunosorbent Assay," *J Clin. Microbiol.* 18(2):287-291 (Aug. 1983).

Cooper, et al., "Epitope mapping of full-length glycoprotein D from HSV-2 reveals a novel $CD4^+$ CTL epitope located at the transmembrane-cytoplasmic junction," *Cell Immunol.* 239:113-120 (2006).

Corbel, et al., "Latest developments and in vivo use of the Tet system: ex vivo and in vivo delivery of tetracycline-regulated genes," *Current Opinion in Biotechnology* 13:448-452 (2002).

Corey, et al., "Infections With Herpes Simplex Viruses," *N. Eng. J. Med.* 314:749-757 (1986).

Davido, et al., "Role of Cis-Acting Sequences of the ICPO Promoter of Herpes Simplex Virus Type 1 in Viral Pathogenesis, Latency and Reactivation,"*J. General Virology* 77:1853-1863 (1996).

DeLuca, et al., "Physical and Functional Domains of the Herpes Simplex Virus Transcriptional Regulatory Protein ICP4," *J. Virol.* 62(3):732-743 (Mar. 1988).

Deuschle, et al., "Tetracycline-Reversible Silencing of Eukaryotic Promoters," *Mol. And Cel. Biol.* 15:1907-1914 (Apr. 1995).

Dolan, et al., "The Genome Sequence of Herpes Simplex Virus Type 2," *J. Virol.* 72(3):2010-2021 (Mar. 1998).

Dudek, et al., "Replication-defective viruses as vaccines and vaccine vectors," *Virology* 344:230-239 (2006).

Fleming, et al., "Herpes Simplex Virus Type 2 in the United States, 1976 to 1994," *N. Eng. J. Med* 337(16):1105-1111 (1997).

Fox, J.L., "Investigation of Gene Therapy Begins," *Nature Biotechnology* 18:143-144 (Feb. 2000).

Freeman, et al., "Herpes simplex virus 2 infection increases HIV acquisition in men and women: systematic review and meta-analysis of longitudinal studies," *Aids* 20:73-83 (2006).

Glorioso, et al., "Immunogenicity of Herpes Simplex Virus Glycoproteins gC and gB and Their Role in Protective Immunity," *J. Virol.* 50(3):805-812 (Jun. 1984).

Glorioso, et al., "Therapeutic Gene Transfer to the Nervous System Using Viral Vectors," *J. NeuroVirol.* 9:165-172 (2003).

Gossen, et al., "Transcriptional Activation by Tetracyclines in Mammalian Cells," *Science* 268:1766-1769 (Jun. 1995).

Gossen, et al., "Tight Control of Gene Expression in Mammalian Cells by Tetracycline-Responsive Promoters," *Proc. Natl. Acad Sci. USA* 89:5547-5551 (Jun. 1992).

Grammer, et al., "Identification of an HSV-1/HSV-2 Cross-Reactive T Cell Determinant," *J. Immunol.* 145(7):2249-2253 (Oct. 1990).

Gupta, et al., "Genital Herpes," *Lancet* 370:2127-2137 (Dec. 2007).

Handler, et al., "Oligometric Structure of Glycoproteins in Herpes Simplex Virus Type 1," *J. Virol.* 70(9):6067-6075 (Sep. 1996).

Hennighausen, et al., "Conditional Gene Expression in Secretory Tissues and Skin of Transgenic Mice Using the MMTV-LTR and the Tetracycline Responsive System," *J. Cell. Biochem* 59:463-472 (1995).

Heur, et al., "Tet Repressor-*tet* Operator Contacts Probed by Operator DNA-modification Interference Studies,"*J. Mol. Biol.* 202:407-415 (1988).

Hillen, et al., "Mechanisms Underlying Expression of TN10 Encoded Tetracycline Resistance," *Ann. Rev. Microbiol.* 48:345-369 (1994).

Hirsch, "Herpes Simplex Virus," p. 1144-1153. In G.L. Mandell, R.G.J. Douglas and J.E. Bennett (ed.), Principles and practice of infectious diseases. Churchill Livingstone Inc., New York (1990).

Honess, et al., "Type Specific and Type Common Antigens in Cells Infected with Herpes Simplex Virus Type 1 and on the Surfaces of Naked and Enveloped Particles of the Virus," *J. gen. Virol.* 22:159-169 (1974).

Hosken, et al., "Diversity of the $CD8^+$ T-Cell Response to Herpes Simplex Virus Type 2 Proteins among Persons with Genital Herpes," *J. Virol.* 80(11):5509-5515 (Jun. 2006).

Jacobs, et al., "HSV-1-Based Vectors for Gene Therapy of Neurological Diseases and Brain Tumors: Part I. HSV-1 Structure, Replication and Pathogenesis," *Neoplasia* 1(5):387-401 (1999).

Jacobs, et al., "HSV-1-Based Vectors for Gene Therapy of Neurological Diseases and Brain Tumors: Part II. Vector Systems and Applications," *Neoplasia* 1(5):402-416 (1999).

Johnson, et al., "Herpes Simplex Virus Glycoprotein D is Recognized as Antigen by $CD4^{+\ and\ CD8+}$ T Lymphocytes from Infected Mice," *J. Immunol.* 145(2):702-710 (Jul. 1990).

Jones, et al., "Vaccination Strategies to Prevent Genital Herpes and Neonatal Herpes Simplex Virus (HSV) Disease," *Herpes* 11(1):12-17 (2004).

(56) References Cited

OTHER PUBLICATIONS

Kim, et al., "Immunodominant Epitopes in Herpes Simplex Virus Type 2 Glycoprotein D are Recognized by CD4 Lymphocytes from Both HSV-1 and HSV-2 Seropositive Subjects," *J. Immunol.* 181:6604-6615 (2008).
Kim, et al., "Tetracycline Repressor-Regulated Gene Repression in Recombinant Human Cytomegalovirus," *J. Virol.* 69(4):2565-2573 (1995).
Kmiec, et al., "Investigators Have Been Searching for Ways to Add Corrective Genes to Cells Harboring Defective Genes. A Better Strategy Might be to Correct the Defects," *American Scientist* 87:240-247 (May 1999).
Knopf, et al., "Evaluation of the T-REx™ transcription switch for conditional expression and regulation of HSV-1 vectors," *Virus Genes* 36:55-66 (2008).
Koelle, et al., "Herpes Simplex: Insights on Pathogenesis and Possible Vaccines," *Annu. Rev. Med* 59:381-395 (2008).
Koelle, et al., "Recent Progress in Herpes Simplex Virus Immunobiology and Vaccine Research," *Clin. Microbiol. Rev.* 16(1):96-113 (Jan. 2003).
Koelle, et al., "Prospects for Developing an Effective Vaccine Against Ocular Herpes Simplex Virus Infection," *Curr. Eye Res.* 30:929-942 (2005).
Koelle, et al., "Herpes Simplex Virus Infection of Human Fibroblasts and Keratinocytes Inhibits Recognition by Cloned CD8+ Cytotoxic T Lymphocytes," *J. Clin. Invest.* 91:961-968 (Mar. 1993).
Kousoulas, et al., "Antibody-Resistant Mutations in Cross-Reactive and Type-Specific Epitopes of Herpes Simplex Virus 1 Glycoprotein B Map in Separate Domains," *Virology* 166:423-431 (1988).
Lakeman, etal., "Analysis of DNA From Recurrent Genital Herpes Simplex Virus Isolates by Restriction Endonuclease Digestion," *Sex. Transm. Dis.* 13:61-66 (1986).
Latchman, et al., "Herpes Simplex Virus Vectors for Gene Delivery to a Variety of Different Cell Types,"*Curr. Gene Ther.* 2:415-426 (2002).
Leib, et al., "Immediate-Early Regulatory Gene Mutants Define Different Stages in the Establishment and Reactivation of Herpes Simplex Virus Latency," *J. Virol.* 63(2):759-768 (Feb. 1989).
Lewandowski, et al., "Evidence that deficient IFN-γ production is a biological basis of herpes simplex virus type-2 neurovirulence," *J. Neuroimmunol.* 81:66-75 (1998).
Liesegang, "Herpes Simplex Virus Epidemiology and Ocular Importance," *Cornea* 20(1):1-13 (2001).
Looker, et al., "A systematic review of the epidemiology and interaction of herpes simplex virus types 1 and 2," *Sex. Transm. Infect.* 81:103-107 (2005).
Lu, et al., "High Level Expression of Glycoprotein D by a Dominant-Negative HSV-1 Virus Augments its Efficacy as a Vaccine against HSV-1 Infection," *J. Invest. Dermatol.* 129:1174-1184 (2009).
Martinez, et al., "The Conserved Helicase Motifs of the Herpes Simplex Virus Type 1 Origin-Binding Protein UL9 Are Important for Function," Journal of Virology 66(11):6735-6746 (Nov. 1992).
Martuza, et al., "Experimental Therapy of Human Glioma by Means of a Genetically Engineered Virus Mutant," *Science* 252:854-856 (1991).
McGeoch, et al., "The Complete DNA Sequence of the Long Unique Region in the Genome of Herpes Simplex Virus Type 1,"*J. Gen. Virol.* 69:1531-1574 (1988).
McGeoch, et al., "Complete DNA Sequence of the Short Repeat Region in the Genome of Herpes Simplex Virus Type 1," *Nuc. Acids Res.* 14(4):1727-1745 (1986).
McGeoch, et al., "Comparative Sequence Analysis of the Long Repeat Regions and Adjoining Parts of the Long Unique Regions in the Genomes of Herpes Simplex Viruses Types 1 and 2," *J. Gen. Virol.* 72:3057-3075 (1991).
McGeoch, et al., "DNA sequence of the region in the genome of herpes simplex virus type 1 containing the exonuclease and neighbouring genes," *Nucl. Acid Res.* 14(8):3435-48 (1986).
Mertz, et al., "Risk Factors for the Sexual Transmission of Genital Herpes," *Ann. Intern. Med.* 116:197-202 (1992).

Mikloska, et al., "Herpes simplex virus type 1 glycoproteins gB, gC and gD are major targets for CD4 T-lymphocyte cytotoxicity in HLA-DR expressing human epidermal keratinocytes," *J. gen. Virol.* 79:353-361 (1998).
Mikloska, et al., "Monophosphoryl Lipid A and QS21 Increase CD8 T Lymphocyte Cytotoxicity to Herpes Simplex Virus-2 Infected Cell Proteins 4 and 27 Through IFN-1γ and IL-12 Production," *J. Immunol.* 164:5167-5176 (2000).
Minson, et al., "An Analysis of the Biological Properties of Monoclonal Antibodies against Glycoprotein D of Herpes Simplex Virus and Identification of Amino Acid Substitutions that Confer Resistance to Neutralization,"*J. gen. Virol.* 67:1001-1013 (1986).
Morrison, et al., "Influence of Mucosal and Parenteral Immunization with a Replication-Defective Mutant of HSV-2 on Immune Responses and Protection from Genital Challenge," *Virology* 243:178-187 (1998).
Muller, "Binding of the Herpes Simplex Virus Immediate-Early Gene Product ICP4 to Its Own Transcription Start Site,"*J. Virol.* 61(3):858-865 (Mar. 1987).
Nagot, et al., "Reduction of HIV-1 RNA Levels with Therapy to Suppress Herpes Simplex Virus," *N. Engl. J. Med.* 356(8):790-799 (Feb. 2007).
No, et al., "Ecdysone-Inducible Gene Expression in Mammalian Cells and Transgenic Mice,"*Proc. Natl. Acad Sci. USA* 93:3346-3351 91996).
Palmer, et al., "Development and Optimization of Herpes Simplex Virus Vectors for Multiple Long-Term Gene Delivery to the Peripheral Nervous System," *J. Virol.* 74(12):5604-5618 (Jun. 2000).
Para, et al., "Potent Neutralizing Activity Associated with Anti-Glycoprotein D Specificity Among Monoclonal Antibodies Selected for Binding to Herpes Simplex Virions," *J. Virol.* 55(2):483-488 (Aug. 1985).
Pereira, "Use of monoclonal antibodies to HSV-1 and HSV-2 for serological analysis of the viral glycoproteins," *Dev. Biol. Stand.* 52:115-131 (1982).
Pereira, et al., "Type-Common and Type-Specific Monoclonal Antibody to Herpes Simplex Virus Type 1," *Infect. Immun.* 29(2):724-732 (Aug. 1980).
Perry, et al., "Characterization of the IE110 Gene of Herpes Simplex Virus Type 1," *J. Gen Virol.* 67:2365-2380 (1986).
Postle, et al., "Nucleotide Sequence of the Repressor Gene of the TN10 Tetracycline Resistance Determinant," *Nuc. Acids Res.* 12(12):4849-4863 (1985).
Rivera, et al., "A Humanized System for Pharmacologic Control of Gene Expression," *Nature Medicine* 2(9):1028-1032 (1996).
Roberts, et al., "Direct Correlation between a Negative Autoregulatory Response Element at the Cap Site of the Herpes Simplex Virus Type 1 IE175 (α4) Promoter and a Specific Binding Site for the IE175 (ICP4) Protein," *J. Virol.* 62(11):4307-4320 (Nov. 1988).
Roizman, et al., "Herpes Simplex Viruses and Their Replication," Chapter 72, pp. 2399-2459; D.M. Knipe (ed.), Fields Virology, 4th ed. Lippincott Williams & Wilkins, Philadelphia, PA. (2001).
Ross, et al., "Gene Therapy in the United States: A Five-Year Status Report," *Human Gene Therapy* 7:1781-1790 (Sep. 1996).
Scarpini, et al., "Latency Associated Promoter Transgene Expression in the Central Nervous System After Stereotaxic Delivery of Replication-Defective HSV-1-Based Vectors," *Gene Therapy* 8:1057-1071(2001).
Schmeisser, et al., "Tetracycline-Regulated Gene Expression in Replication-Incompetent Herpes Simplex Virus Vectors," *Hum. Gene Ther.* 13:2113-2124 ( Dec. 2002).
Schmidt, et al., "Reinfection is an Uncommon Occurrence in Patients with Symptomatic Recurrent Genital Herpes," *J. Infect. Dis.* 149(4):645-646 (Apr. 1984).
Stanberry, "Clinical Trials of Prophylactic and Therapeutic Herpes Simplex Virus Vaccines," *Herpes* 11 (*Suppl 3*):161A-169A (2004).
Stanberry, et al., "Prospects for Control of Herpes Simplex Virus Disease through Immunization," *Clin. Infect. Dis.* 30:549-566 (2000).
Stanberry, et al., "Glycoprotein-D-Adjuvant Vaccine to Prevent Genital Herpes," *N. Engl. J. Med* 347(21):1652-1661 (Nov. 2002).

(56) References Cited

OTHER PUBLICATIONS

Starr, et al., "Long-term persistence of defective HSV-1 vectors in the rat brain is demonstrated by reactivation of vector gene expression," *Gene Ther.* 3:615-623 (1996).
Stow, et al., "Isolation and Characterization of a Herpes Simplex Virus Type 1 Mutant Containing a Deletion within the Gene Encoding the Immediate Early Polypeptide Vmw110," *J. gen. Virol.* 67:2571-2585 (1986).
Tigges, et al., "Human CD8+ Herpes Simplex Virus-Specific Cytotoxic T-Lymphocyte Clones Recognize Diverse Virion Protein Antigens," *J. Virol.* 66(3):1622-1634 (Mar. 1992).
Verma, et al., "Gene Therapy-Promises, Problems, and Prospects," *Nature* 389:239-242 (Sep. 1997).
Wang, et al., "A Regulatory System for Use in Gene Transfer," *Proc. Natl. Acad Sci. USA* 91:8180-8184 (1994).
Wang, et al., "Mammary Hyperplasia and Carcinoma in MMTV-Cyclin D1 Transgenic Mice," *Nature* 369:669-671 (Jun. 1994).
Whitley, et al., "Herpes Simplex Viruses," *Clin. Infect. Dis.* 26:541-53; quiz 554-55 (1998).
Wissman, et al., "Saturation Mutagenesis of the Tn10-Encoded *tet* Operator $O_1$; Identification of Base-Pairs Involved in Tet Repressor Recognition," *J. Mol. Biol.* 202:397-406 (1988).
Xu, et al., "Seroprevalence and Coinfection with Herpes Simplex Virus Type 1 and Type 2 in the United States, 1988-1994," *J. Infect. Dis.* 185:1019-1024 (2002).
Yao, et al., "A Novel Anti-Herpes Simplex Virus Type 1—Specific Herpes Simplex Virus Type 1 Recombinant," *Hum. Gene Ther.* 10:1811-1818 (Jul. 1999).
Yao, et al., "A Novel Tetracycline-Inducible Viral Replication Switch," *Hum. Gene Ther.* 10:419-427 (Feb. 1999).
Yao, et al., "Inhibition of herpes simplex virus type 2 (HSV-2) viral replication by the dominant negative mutant polypeptide of HSV-1 origin binding protein," *Antiviral Res.* 53:127-33 (2002).
Yao, et al., "An Activity Specified by the Osterosarcoma Line U2OS Can Substitute Functionally for ICP0, a Major Regulatory Protein of Herpes Simplex Virus Type 1," *J. Virol.* 69(10):6249-6258 (1995).
Yao, et al., "Tetracycline Repressor, tetR, rather than the tetR-Mammalian Cell Transcription Factor Fusion Derivatives, Regulates Inducible Gene Expression in Mammalian Cells," *Human Gene Ther.* 9:1939-1950 (Sep. 1998).
Yao, et al., "Physical Interaction Between the Herpes Simplex Virus Type 1 Immediate-Early Regulatory Proteins ICP0 and ICP4," *J. Virol.* 68:8158-8168 (1994).
Yao, et al., "Highly Efficient Regulation of Gene Expression by Tetracycline in a Replication-Defective Herpes Simplex Viral Vector," *Mol. Ther.* 13(4):1133-1141 (Jun. 2006).
Zarling, et al., "Human Cytotoxic T Cell Clones Directed Against Herpes Simplex Virus-Infected Cells,"*J. Immunol.* 136(12):4669-4673 (Jun. 1986).
International Search Report for PCT/US2010/061320 filed Dec. 20, 2010.
Written Opinion of the International Searching Authority for PCT/US2010/061320 filed Dec. 20, 2010.
International Preliminary Report on Patentability for PCT/US2010/061320 filed Dec. 20, 2010.
Office Action mailed Jun. 12, 2007 in the prosecution of U.S. Appl. No. 11/117,375.
Response to Office Action of Jun. 12, 2007 in the prosecution of U.S. Appl. No. 11/117,375, filed by Applicant on Sep. 12, 2007.
Office Action mailed Nov. 27, 2007 in the prosecution of U.S. Appl. No. 11/117,375.
Response to Office Action of Nov. 27, 2007 in the prosecution of U.S. Appl. No. 11/117,375, filed by Applicant on Feb. 24, 2008.
Appeal Brief filed by Applicant on May 27, 2008 in the prosecution of U.S. Appl. No. 11/117,375.
Office Action mailed Oct. 15, 2008 in the prosecution of U.S. Appl. No. 11/117,375.
Response to Office Action of Oct. 15, 2008 in the prosecution of U.S. Appl. No. 11/117,375, filed by Applicant on Feb. 24, 2008.
Notice of Noncompliant Amendment mailed Apr. 21, 2009 in the prosecution of U.S. Appl. No. 11/117,375.
Response to Notice of Noncompliant Amendment of Apr. 21, 2009 in the prosecution of U.S. Appl. No. 11/117,375, filed by Applicant on May 4, 2009.
Office Action mailed Nov. 9, 2009 in the prosecution of U.S. Appl. No. 11/117,375.
Response to Office Action of Nov. 9, 2009 in the prosecution of U.S. Appl. No. 11/117,375, filed by Applicant with RCE on Feb. 10, 2010.
Office Action mailed Aug. 5, 2010 in the prosecution of U.S. Appl. No. 11/117,375.
Response to Office Action of Aug. 5, 2010 in the prosecution of U.S. Appl. No. 11/117,375, filed by Applicant on Nov. 10, 2010.
Office Action mailed Jan. 20, 2011 in the prosecution of U.S. Appl. No. 11/117,375.
Response to Office Action of Jan. 20, 2011 filed in the prosecution of U.S. Appl. No. 11/117,375 on May 20, 2011 along with an Rce.
Declaration Under 37 CFR §1.132 filed in the prosecution of U.S. Appl. No. 11/117,375 on May 20, 2011.
Office Action mailed Aug. 16, 2011 in the prosecution of U.S. Appl. No. 11/117,375.
Appeal Brief filed by Applicant on Nov. 26, 2011 for U.S. Appl. No. 11/117,357.
Examiner's Answer mailed by the USPTO on Feb. 2, 2012 for U.S. Appl. No. 11/117,357.
English translation of Office Action sent Apr. 24, 2013 for corresponding Chinese application 201080058385.7, with Search Report and claims currently pending in China attached.
Brinster, et al., "Regulation of metallothionein-thymidine kinase fusion plasmids injected into mouse eggs," *Nature* 296(4):39-42 (Mar. 1982).
Brown, et al., "*lac* Repressor Can Regulate Expression from a Hybrid SV40 Early Promoter Containing a *lac* Operator in Animal Cells," *Cell* 49:603-612 (Jun. 1987).
Ghosh, et al., "Expanding Adeno-associated Viral Vector Capacity: A Tale of Two Vectors," *Biotechnology and Genetic Engineering Reviews* 24:165-178 (2007).
Labow, et al., "Conversion of the *lac* Repressor into an Allosterically Regulated Transcriptional Activator for Mammalian Cells," *Mol. Cell. Biol.* 10(7):3343-3356 (Jul. 1990).
Le, et al., "Inducible Expression of Cre Recombinase in the Retinal Pigmented Epithelium," *Investigative Ophthalmology & Visual Science* 49(3):1248-1253 (2008).
Nover, in *Heat Shock Response*, pp. 167-220, CRC, Fla. (1991).
Radomska, et al., "Transgenic targeting with regulatory elements of the human *CD34* gene," *Blood* 100(13):4410-4419 (Dec. 2002).
Kemble G, et al. Herpes simplex vaccines. In: Arvin A, Campadelli-Fiume G, Mocarski E, et al., editors. Human Herpesviruses: Biology, Therapy, and Immunoprophylaxis. Cambridge: Cambridge University Press; 2007. Chapter 69. Available from: http://www.ncbi.nlm.nih.gov/books/NBK47451/?report=printable.

\* cited by examiner

```
ATGGGAGAGGCGTCGCTGCCGGCCCAGGCCGCCGAGACGGAGGAGGTGGGTCTTTTGTCGAA
AAATACCTCCGGTCCGATGTCGCGCCGGCGGAAATTGTCGCGCTCATGCGCAACCTCAACAG
CCTGATGGGACGCACGCGGTTTATTTACCTGGCGTTGCTGGAGGCCTGTCTCCGCGTTCCCA
TGGCCACCCGCAGCAGCGCCATATTTCGGCGGATCTATGACCACTACGCCACGGGCGTCATC
CCCACGATCAACGTCACCGGAGAGCTGGAGCTCGTGGCCCTGCCCCCCACCCTGAACGTAAC
CCCCGTCTGGGAGCTGTTGTGCCTGTGCAGCACCATGGCCGCGCGCCTGCATTGGGACTCGG
CGGCCGGGGATCTGGGAGGACCTTCGGCCCCGATGACGTGCTGGACCTACTGACCCCCCAC
TACGACCGCTACATGCAGCTGGTGTTCGAACTGGGCCACTGTAACGTAACCGACGGACTTCT
GCTCTCGGAGGAAGCCGTCAAGCGCGTCGCCGACGCCCTAAGCGGCTGTCCCCGCGCGGGT
CCGTTAGCGAGACGGACCACGCGGTGGCGCTGTTCAAGATAATCTGGGGCGAACTGTTTGGC
GTGCAGATGGCCAAAAGCACGCAGACGTTTCCCGGGCGGGGCGCGTTAAAAACCTCACCAA
ACAGACAATCGTGGGGTTGTTGGACGCCCACCACATCGACCACAGCGCCTGCCGGACCCACA
GGCAGCTGTACGCCCTGCTTATGGCCCACAAGCGGGAGTTTGCGGGCGCGCTTCAAGCTA
CGCGTGCCCGCGTGGGGCGCTGTTTGCGCACGCACTCATCCAGCGCCAACCCCAACGCTGA
CATCATCCTGGAGGCGGCGCTGTCGGAGCTCCCCACCGAGGCCTGGCCCATGATGCAGGGGG
CGGTGAACTTTAGCACCCTATAA
```

FIG. 10

SEQUENCE LISTING

```
<160> NUMBER OF SEQ ID NOS: 5

<210> SEQ ID NO 1
<211> LENGTH: 19
<212> TYPE: DNA
<213> ORGANISM: Escherichia coli

<400> SEQUENCE: 1
tccctatcag tgatagaga                                                    19

<210> SEQ ID NO 2
<211> LENGTH: 953
<212> TYPE: DNA
<213> ORGANISM: human herpesvirus 1

<400> SEQUENCE: 2
atgggagagg cgtcgctgcc ggcccaggcc gccgagacgg aggaggtggg tcttttgtcg       60
aaaaatacct ccggtccgat gtcgcgccgg cggaaattgt cgcgctcatg cgcaacctca      120
acagcctgat gggacgcacg cggtttattt acctggcgtt gctggaggcc tgtctccgcg      180
ttcccatggc caccccgcagc agcgccatat tcggcggat ctatgaccac tacgccacgg      240
gcgtcatccc cacgatcaac gtcaccggag agctggagct cgtggccctg cccccccaccc     300 tgaacgtaac ccccgtctgg gagctgttgt gcctgtgcag caccatggcc gcgcgcctgc     360
attgggactc ggcggccggg ggatctggga ggaccttcgg ccccgatgac gtgctggacc      420
tactgacccc ccactacgac cgctacatgc agctggtgtt cgaactgggc cactgtaacg      480
taaccgacgg acttctgctc tcggaggaag ccgtcaagcg cgtcgccgac gccctaagcg     540
gctgtccccc gcgcgggtcc gttagcgaga cggaccacgc ggtggcgctg ttcaagataa      600 tctgggcga actgtttggc gtgcagatgg ccaaaagcac gcagacgttt cccggggcgg      660
ggcgcgttaa aaacctcacc aaacagacaa tcgtggggtt gttggacgcc caccacatcg      720
accacagcgc ctgccggacc cacaggcagc tgtacgccct gcttatggcc cacaagcggg     780
agtttgcggg cgcgcgcttc aagctacgcg tgcccgcgtg ggggcgctgt ttgcgcacgc      840
actcatccag cgccaacccc aacgctgaca tcatcctgga ggcggcgctg tcggagctcc     900
ccaccgaggc ctggcccatg atgcaggggg cggtgaactt tagcaccccta taa            953
```

```
<210> SEQ ID NO 3
<211> LENGTH: 15
<212> TYPE: DNA
<213> ORGANISM: human herpesvirus 1

<400> SEQUENCE: 3
atcgtccaca cggag                                                      15

<210> SEQ ID NO 4
<211> LENGTH: 22
<212> TYPE: DNA
<213> ORGANISM: human herpesvirus 2

<400> SEQUENCE: 4
gctcgagtgc gaaaaaacgt tc                                              22

<210> SEQ ID NO 5
<211> LENGTH: 17
<212> TYPE: DNA
<213> ORGANISM: human herpesvirus 2

<400> SEQUENCE: 5
cggggcgctc ggctaac                                                    17
```

HERPES SIMPLEX VIRUS VACCINES

CROSS REFERENCE TO RELATED APPLICATIONS

The present application is US national stage of international application PCT/US2010/061320, which had an international filing date of Dec. 20, 2010, and claims the benefit of U.S. provisional application 61/288,836, filed on Dec. 21, 2009 the contents of which is hereby incorporated by reference in its entirety. The international application was published in English under PCT Article 21(2) on Jun. 30, 2011.

FIELD OF THE INVENTION

The present invention is primarily concerned with vaccines that can be used to immunize patients against Herpes Simplex Virus type 2 (HSV-2) infections associated with chronic genital ulcers. The vaccine utilizes a replication defective HSV-2 virus that has been engineered to express high levels of HSV-2 glycoprotein D antigen (gD2). In preferred embodiments, the HSV-2 virus also expresses one or more immunomodulating genes, such as IL15 and/or HSV-1 or HSV-2 major antigens such as gB or gC.

BACKGROUND OF THE INVENTION

Herpes Simplex Viruses (HSV) and HSV Infections

Herpes simplex virus 2 (HSV-2) is the primary cause of genital ulcer disease. It can cause both an acute, productive infection and a long-term latent infection characterized by unpredictable periodic recurrences (66). Apart from causing lifelong, recurrent genital ulcers, HSV infections are a major concern in AIDS patients. It has been documented that genital HSV-2 infection triples the risk for sexually acquiring HIV infection (20), and in Africa, this increase in risk may contribute to 25-35% of incident HIV infections (1).

Although the severity and duration of most symptomatic HSV primary infections can be reduced by oral or intravenous treatment with acyclovir, valacyclovir, or famciclovir, antiviral therapy neither prevents the establishment of latent infection from primary infection nor reduces subsequent recurrences (66). The continued spread of genital herpes in the United States over the past two decades (19) and the increasing incidence of HSV resistant to current antiviral medications suggest that there is a need for safe and efficacious vaccines against HSV infections (31, 60). In addition, the finding that HSV suppressive therapy leads to a significant reduction in levels of HIV in the genital mucosa and plasma of women infected with both HSV-2 and HIV (52) suggests that an effective HSV vaccine may also have major implications in control of HIV infection (1, 31).

HSV-2 Glycoprotein D (gD2)

HSV glycoprotein D (gD) is one of the most predominant viral antigens expressed on the surface of infected cells (21) and as well as on the viral envelope (24). gD is essential for the entry of the virus into cells and is a major target for neutralizing antibodies against HSV infection (12, 49, 53). Moreover, gD is the predominant viral target for CD4$^+$ T cells including CD4$^+$ T cell cytotoxicity and CD8$^+$ T cells in human and murine models of HSV infection (27, 28, 30, 34, 47, 65, 75). For these reasons, gD has been a major focus for HSV subunit vaccine development (32, 60).

In a phase 3 clinical trial, Stanberry, et al., showed that vaccination with recombinant gD from HSV-2 (gD2), in combination with adjuvant AS04, provided 73-74% efficacy in protecting against the development of genital herpes disease in HSV-seronegative women (62). No significant efficacy was observed, however, in men and in subjects who were seropositive for HSV-1. Although gD2-specific humoral and CD4+ T cell responses were detected in the immunized hosts, it is not clear whether gD2/AS04 was effective in eliciting a CD8+ T cell response (31, 32). This study suggests that there is a need for an HSV vaccine that elicits a broader humoral, as well as CD4 and CD8 T-cell, response to both gD2 and other HSV viral antigens (29, 31, 32).

Viral Vaccines

It is well documented that live viral vaccines capable of de novo synthesis of immunogens in the host induce a broader and more durable immune response than vaccines consisting of only peptides or proteins. Various forms of replication-defective HSV and neuroattenuated, replication-competent mutants have been developed and tested as potential in vaccines against HSV infection (U.S. Pat. No. 7,223,411; (18)).

Because both replication-defective viruses and neuroattenuated mutants can co-replicate with wild-type virus or become replication-competent in the context of wild-type virus, their use as a vaccine in humans poses a safety concern, particularly in individuals who harbor latent HSV infection (33). The observation that replication-defective HSV-1 mutants can reactivate the latent HSV-1 immediate-early promoter in the rodent brain has raised additional safety concerns about the possibility of such recombinants triggering outbreaks of productive viral infections in latently infected individuals (63). Thus, a desirable replication-defective recombinant HSV vaccine should not only possess the ability to express a broad spectrum of virus-encoded antigens but should also encode a unique function that can prevent lytic infection of wild-type HSV when encountered within the same cells. Such a safety mechanism would minimize the potential outbreak of the vaccine virus caused by the recombination of the vaccine vector with wild type virus in the host.

SUMMARY OF THE INVENTION

In general, the present invention is based upon the use of tetracycline gene-switch technology (T-REx, Invitrogen) (73) and a dominant-negative mutant form of the HSV-1 UL9 polypeptide, e.g., UL9-C535C, to develop a safe and effective recombinant viral vaccine against HSV-2 infection.

In its first aspect, the invention is directed to a replication-defective, dominant-negative Herpes simplex virus 2 (HSV-2) recombinant virus. The genome of the virus has, at least, a first sequence encoding a first HSV-2 glycoprotein D (gD2) operably linked to a first promoter and, preferably, a second sequence encoding a second HSV-2 gD2 which is operably linked to a second promoter. The promoter(s) are operably linked to a first tetracycline operator (tet-O) sequence and a second tet-O sequence respectively, each of which allows transcription to proceed when free of tet repressor but which blocks transcription when bound by repressor. The genome also includes a third sequence which encodes, at least, a first dominant negative mutant form of the HSV-1 or HSV-2 UL9 protein linked to a third promoter and, preferably, a fourth sequence which encodes a second dominant negative form of the HSV-1 or HSV-2 UL9 protein linked to a fourth promoter. Like the first and second promoters, the third and fourth promoters are each operably linked to a tet-O sequence which, if bound by tet repressor, blocks transcription. In addition, the genome of the virus is characterized by the absence of a sequence encoding a functional ICP0 protein. In order to enhance its antigenicity, the genome should preferably also express immunomodulating genes, such as IL12 or IL15 and/or HSV-1 or HSV-2 major antigens such as gB or gC.

The term "operably linked" refers to genetic elements that are joined together in a manner that enables them to carry out their normal functions. For example, a gene is operably linked to a promoter when its transcription is under the control of the promoter and this transcription results in the production of the product normally encoded by the gene. A tet operator sequence is operably linked to a promoter when the operator blocks transcription from the promoter in the presence of bound tet repressor and but allows transcription in the absence of the repressor. The term "recombinant" refers to a virus that has nucleic acid sequences that were, at some time, formed by the recombination of nucleic acid sequences and sequence elements and the introduction of these recombined sequences into the virus or into an ancestor virus.

Preferably, the promoters used are those that have a TATA element and the tet operator sequences linked to the promoters have two op2 repressor binding sites joined together by between two and twenty linking nucleotides. The positioning of the operator sequence is important to achieve effective control over the promoter. Specifically, the first nucleotide in the operator sequence must be located between six and twenty-four nucleotides 3' to the last nucleotide in the TATA element. Structural sequences encoding, for example gD or a dominant-negative mutant polypeptide of UL9, would lie 3' to the operator. Among specifically preferred promoters are the hCMV immediate early promoter and HSV-1 or HSV-2 immediate early promoters. Especially preferred is the HSV-1 or HSV-2 ICP4 promoter.

In another aspect, the invention is directed to a vaccine that can be used prophylactically or therapeutically against HSV expression and which comprises one or more of the recombinant viruses described above in unit dose form. The term "unit dose form" refers to a single drug administration entity such as a tablet or capsule. Preferably the "unit dose form" will be a solution in which drug is dissolved at a concentration that provides a therapeutic or prophylactic effect when a selected volume (unit dose) is administered to a patient by injection and will be found within an injection vial. Based on the effective dose used in mice ($2 \times 10^6$ PFU), it is believed that the minimal effective dose in human should be about $1 \times 10^7$ pfu. Thus, a unit dose should have at least this amount of virus, with $1 \times 10^7 - 1 \times 10^9$ pfu being typical. Vaccines may be stored in a lyophilized form and reconstituted in a pharmaceutically acceptable carrier prior to administration. Alternatively, preparations may be stored in the vehicle itself. The volume of a single dose of the vaccine will vary but, in general, should be between about 0.1 ml and 10 ml and, more typically, between about 0.2 ml and 5 ml.

The invention also includes methods of immunizing patients against HSV-1 or HSV-2 infection and the conditions resulting from such infection (e.g., genital Herpes ulcers) by administering to the patients the vaccines described above. The vaccines may also be given to patients that have been infected to prevent or reduce outbreaks of the virus. Any method for administering a vaccine to a patient which does not result in the destruction of virus is compatible with the present invention. Generally, administration will be by parenteral means such as by intramuscular or intravenous injection. The dosage and scheduling of administration of vaccines can be determined using methods that are routine in the art. The preparations may be administered in either single or multiple injections.

BRIEF DESCRIPTION OF THE DRAWINGS

FIG. 1A shows a schematic diagram of plasmids used for the construction of dominant-negative and replication-defective HSV-2 recombinants N2-C535C and CJ2-gD2. Plasmid pHSV-2/ICP0 is a plasmid containing the HSV-2 ICP0 sequences covering 268 bp upstream of the HSV-2 ICP0 open reading frame (grey box) to 40 bp downstream of the poly A signal of ICP0 coding sequences. pHSV2.ICP0-V was constructed by replacing the Xho I-ICP0 DNA fragment containing sequences with an Xho I-containing multiple cloning sequence (MCS). pHSV2.ICP0-lacZ was created by inserting the LacZ gene (striped box) into the MCS region of pHSV2.ICP0-V. p02lacZ-TOC535C was constructed by replacing the indicated lacZ-containing fragment of pHSV2.ICP0-lacZ with DNA sequences encoding UL9-C535C (black box) under control of the tetO-containing hCMV major immediate-early promoter (line box, CMVTO). p02lacZTO-gD2.C535C was constructed by replacing the indicated SnaB I/Pst I fragment of p02lacZTO-C535C with DNA sequences encoding gD2 gene (gradient box) under control of the tetO-containing HSV-1 immediate-early ICP4 promoter (open box, ICP4TO).

FIG. 1B shows a schematic diagram of genomes of wild-type HSV-2, an HSV-2 ICP0 null mutant (N2-lacZ), N2-C535C and CJ2-gD2. UL and US represent the unique long and unique short regions of the HSV-2 genome, respectively, which are flanked by their corresponding inverted repeat regions (open boxes). The replacement of both copies of the ICP0 coding sequences with the lacZ gene in N2-lacZ and with DNA sequences (1) encoding UL9-C535C under control of the tetO-bearing hCMV major immediate-early promoter in N2-C535C, and (2) encoding both UL9-C535C and gD2 under the indicated tetO-bearing promoters in an opposite orientation are shown below the expanded ICP0 coding sequences of the HSV-2 genome.

In FIG. 2A, Vero cells in duplicate were either mock-infected or infected with wild-type HSV-2, N2-lacZ, N2-C535C, or CJ2-gD2 at an MOI of 10 PFU/cell. Infected cell extracts were prepared at 9 h post-infection. In FIG. 2B, Vero cells were infected with wild type HSV-1 strain KOS, CJ9-gD, wild-type HSV-2, or CJ2-gD2 at an MOI of 10 PFU/cell. Infected cell extracts were prepared at 9 h post-infection. Proteins in infected cell extracts were resolved on SDS-PAGE, followed by immunoblotting with polyclonal antibodies against HSV-1 gD (R45), UL9, or monoclonal antibodies specific for ICP27 and gB (Santa Cruz).

FIG. 3 shows the regulation of gD2 and UL9-C535C expression by tetR in CJ2-gD2-infected VCEP4R-28 cells. VCEP4R-28 cells were seeded at $5 \times 10^5$ cells per 60-mm dish. At 40 h after seeding, cells in duplicate were either mock-infected or infected with wild-type HSV-2 or CJ2-gD2 at an MOI of 10 PFU/cell in either the presence or the absence of tetracycline. Infected cell extracts were prepared at 9 h post-infection followed by immunoblotting with polyclonal antibodies against HSV gD and UL9, and a monoclonal antibody specific for ICP27.

In FIG. 4A, Vero cells in triplicate were infected with either wild-type HSV-2 strain 186 at an MOI of 2 PFU/cell, 186 at an MOI of 2 PFU/cell and CJ2-gD2 at an MOI of 5 PFU/cell, or 186 at an MOI of 2 PFU/cell and N2-lacZ at an MOI of 5 PFU/cell. In FIG. 4B, Vero cells were either singly infected with wild-type HSV-2 at an MOI of 5 PFU/cell, co-infected with 186 and CJ2-gD2 at an MOI of 5 PFU/cell for both viruses, or singly infected with 186 at an MOI of 15 PFU/cell, and co-infected with 186 at an MOI of 15 PFU/cell and CJ2-gD2 at an MOI of 5 PFU/cell. Infected cells were harvested at 18 h post-infection and viral titers were determined on Vero cell monolayers. Viral titers are expressed as the mean +/−SD. Numbers on the top of the graph indicate the fold reduction in wild-type virus yield between single infection and co-infection.

FIG. 5A shows disease score at various days after injection and FIG. 5B shows the percetage of mice surviving.

FIGS. 6A and 6B are concerned with the induction of gD2-specific antibodies and HSV-2-neutralizing responses. Female 4- to 6-week-old BALB/c mice were either sham-immunized with DMEM (n=7, 6, 8, 8) or immunized with CJ2-gD2 (n=7, 6, 8, 8), N2-C535C (n=7, 8, 6), or CJ9-gD (n=6, 8, 6) at a dose of $2 \times 10^6$ PFU/mouse, and boosted 2 weeks later. Blood was obtained from the tail veins of mice 4-5 weeks after primary immunization. In FIG. 6A, serum from an individual group of mice was pooled and heat-inactivated. HSV-2-specific neutralizing antibody titers were determined. The results represent average titers±SEM. In FIG. 6B, sera from sham-immunized, CJ2-gD2-, N2-C535C-, or CJ9-gD-immunized mice were incubated with cell extract prepared from U2OS cells transfected with gD2-expressing plasmid p02.4TO-gD2. gD/mouse IgG-specific complexes were precipitated with Protein A, resolved on SDS-PAGE, and probed with a gD-specific polyclonal antibody, R45.

In FIGS. 7A and 7B, sham-immunized and immunized mice were either mock-infected or infected with wild-type HSV-2 s.c. at a dose of $1 \times 10^4$ PFU/mouse at 9-10 weeks post boost immunization (n=3). The CD4+ and CD8+ T cell responses were analyzed on day 5 post-challenge by IFN-γ ELISPOT assays with individually purified CD4+ and CD8+ T cells isolated from the mouse spleen using Dynal mouse CD4- and CD8-negative kits. In FIGS. 7C and 7D, sham-immunized and CJ2-gD2 immunized mice were mock-infected or infected with wild-type HSV-2 at 5-6 weeks post boost immunization followed by IFN-γ ELISPOT assays on day 4 post-infection (n=3). The number of IFN-γ spot-forming cells (SFC) was expressed as the mean±SEM per million CD4+ or CD8+ T cells.

FIG. 8 shows the reduction of challenge HSV-2 vaginal replication in mice immunized with CJ2-gD2. Female 4- to 6-week-old BALB/c mice were randomly assigned to 4 groups of 10 mice each. Mice were either mock-immunized with DMEM or immunized with CJ2-gD2, N2-C535C, or CJ9-gD at a dose of $2 \times 10^6$ PFU/mouse. Mice were boosted after 2 weeks. At 5 weeks, mice were pretreated with medroxyprogesterone and challenged intravaginally with $5 \times 10^5$ PFU of HSV-2 strain G. Vaginal swabs were taken on days 1, 2, 3, 5, and 7 post-challenge. Infectious viruses in swab materials were assessed by standard plaque assay on Vero cell monolayers. Viral titers are expressed as the mean±SEM in individual vaginal swabs.

FIG. 10: FIG. 10 shows the HSV-1 UL9-C535C coding sequence (SEQ ID NO:2). UL9-C535C consists of UL9 amino acids 1-10, a Thr-Met-Gly tripeptide, and amino acids 535 to 851 of UL9 (see Yao, et al. (69)).

DETAILED DESCRIPTION OF THE INVENTION

Figure 1A:
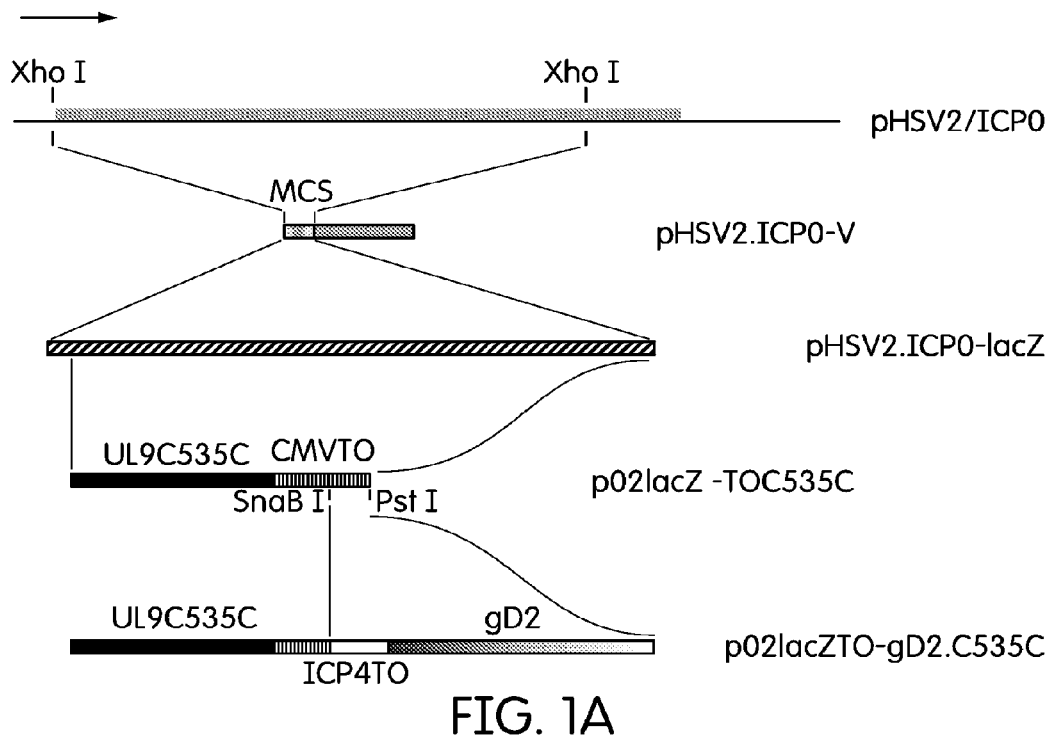
FIGS. 1A and 1B.

The present invention is based upon the concept of using tetracycline gene-switch technology and a dominant-negative mutant polypeptide of HSV-1 UL9 to develop an HSV recombinant virus which is replication defective and capable of inhibiting wild-type HSV infections (dominant-negative). CJ9-gD is a prototype dominant-negative, replication defective HSV-1 recombinant virus and expresses high-levels of HSV-1 major antigen glycoprotein D (gD) independent of HSV viral DNA replication (7). In its most preferred form, the present invention uses a dominant-negative and replication-defective HSV-2 recombinant (CJ2-gD2) that encodes 2 copies of the HSV-2 gD (gD2) gene, driven by the tetO-bearing HSV-1 major immediate-early ICP4 promoter. CJ2-gD2 expresses gD2 as efficiently as wild-type HSV-2 and can exert a powerful trans-inhibitory effect on the replication of wild type HSV-2 in co-infected cells. Immunization with CJ2-gD2 elicits effective HSV-2-specific neutralizing antibody as well as T-cell responses, and offers a complete protection against intravaginal infection by wild-type HSV-2 in mice.

CJ2-gD2 is a more effective vaccine than CJ9-gD in protection against wild-type HSV-2 genital infection and disease. Furthermore, intracerebral injection of a high dose of CJ2-gD2 causes no mortality or morbidity in mice. Collectively, these observations suggest that CJ2-gD2 has advantages over traditional replication-defective virus vaccines and HSV-2 subunit vaccines in protecting against HSV-2 genital infection and disease in humans.

The Tet Operator/Repressor Switch and Recombinant DNA

The present invention is directed to, inter alia, viruses having genes whose expression is regulated by the tetracycline operator and repressor protein. Methods that can be employed to make recombinant DNA molecules containing these elements and DNA sequences have been previously described (see U.S. Pat. No. 6,444,871; U.S. Pat. No. 6,251,640; and U.S. Pat. No. 5,972,650) and plasmids which contain the tetracycline-inducible transcription switch are commercially available (T-REx™, Invitrogen, CA).

An essential feature of the DNA of the present invention is the presence of genes that are operably linked to a promoter, preferably having a TATA element. A tet operator sequence is located between 6 and 24 nucleotides 3' to the last nucleotide in the TATA element of the promoter and 5' to the gene. Virus may be grown in cells that express the tet repressor in order to block gene transcription and allow viral replication. The strength with which the tet repressor binds to the operator sequence is enhanced by using a form of operator which contains two op2 repressor binding sites (each such site having the nucleotide sequence: TCCCTATCAGTGATAGAGA (SEQ ID NO:1)) linked by a sequence of 2-20, preferably 1-3 or 10-13, nucleotides. When repressor is bound to this operator, very little or no transcription of the associated gene will occur. If DNA with these characteristics is present in a cell that also expresses the tetracycline repressor, transcription of the gene that can prevent viral infection will be blocked by the repressor binding to the operator and replication of the virus will occur.

Selection of Promoters and Genes

During productive infection, HSV gene expression falls into three major classes based on the temporal order of expression: immediate-early (α), early (β), and late (γ), with late genes being further divided into two groups, γ1 and γ2. The expression of immediate-early genes does not require de novo viral protein synthesis and is activated by the virion-associated protein VP16 together with cellular transcription factors when the viral DNA enters the nucleus. The protein products of the immediate-early genes are designated infected cell polypeptides ICP0, ICP4, ICP22, ICP27, and ICP47 and it is the promoters of these genes that are preferably used in directing the expression of the recombinant genes discussed herein.

ICP0 plays a major role in enhancing the reactivation of HSV from latency and confers a significant growth advantage on the virus at low multiplicities of infection. ICP4 is the major transcriptional regulatory protein of HSV-1, which activates the expression of viral early and late genes. ICP27 is essential for productive viral infection and is required for efficient viral DNA replication and the optimal expression of viral γ genes and a subset of viral β genes. The function of ICP47 during HSV infection appears to be to down-regulate the expression of the major histocompatibility complex (MHC) class I on the surface of infected cells.

The full length sequence of the HSV-1 genome sequence of the coding region of the HSV-1 UL9-C535C is shown in FIG. 10 (SEQ ID NO:2). The other sequences described for use in recombinant viruses are all well known in the art. For example the full length genomic sequence for HSV-1 may be found as GenBank sequence X14112. The HSV-1 ICP4 sequence may be found as GenBank number X06461; HSV-1 glycoprotein D may be found as GenBank sequence J02217; HSV-2 glycoprotein D may be found as GenBank number K01408; and the HSV-1 UL 9 gene as GenBank sequence M19120 (all of which arc incorporated by reference herein in their entirety).

Inclusion of Tet Repressor and Making of Virus

Sequences for the HSV ICP0 and ICP4 promoters and for the genes whose regulation they endogenously control are well known in the art (43, 44, 56) and procedures for making viral vectors containing these elements have been previously described (see US published application 2005-0266564). These promoters are not only very active in promoting gene expression, they are also specifically induced by VP16, a transactivator released when HSV-1 or HSV-2 infects a cell.

Once appropriate DNA constructs have been produced, they may be incorporated into HSV-2 virus using methods that are well known in the art (see generally Yao et al. (68)).

Immunization Methods

The viruses described herein will be used to immunize individuals and/or patients, typically by injection as a vaccine. The vaccine may be used both prophylactically to prevent HSV-1 or HSV-2 infection or therapeutically to reduce the severity of an HSV-1 or HSV-2 infection that has already occurred. In order make a vaccine, the viruses can be suspended in any pharmaceutically acceptable solution including sterile isotonic saline, water, phosphate buffered saline, 1,2-propylene glycol, polyglycols mixed with water, Ringer's solution, etc. The exact number of viruses to be administered is not crucial to the invention but should be an "effective amount," i.e., an amount sufficient to elicit an immunological response strong enough to inhibit HSV infection. In general, it is expected that the number of viruses (PFU) initially administered will be between $1\times10^7$ and $1\times10^{10}$.

The effectiveness of a dosage, as well as the effectiveness of the overall treatment can be assessed using standard immunological methods to test for the presence of antibodies effective at attacking HSV. Immunological injections can be repeated as many times as desired.

EXAMPLES

The current example describes the creation of an HSV-2 recombinant virus and tests to determine its immunological effects.

1. Materials and Methods

Cells

African Green Monkey Kidney (Vero) cells and the osteosarcoma line U2OS cells were grown and maintained in Dulbecco's Modified Eagle's Medium (DMEM; Sigma Aldrich) supplemented with 10% fetal bovine scrum (FBS) in the presence of 100 U/ml penicillin G and 100 μg/ml streptomycin sulfate (GIBCO, Carlsbad, Calif.) (71). U2OS cells are able to complement functionally for the HSV-1 ICP0 deletion (71). U2CEP4R11 cells are tetR-expressing U2OS cells that were maintained in DMEM plus 10% FBS and hygromycin B at 50 μg/m1 (73). VCEP4R-28 cells are tetR-expressing Vero cells that were maintained in DMEM plus 10% FBS and hygromycin B at 50 μg/ml (73).

Plasmids

Plasmid pHSV2/ICP0 is a pUC19 derived plasmid that encodes the PCR amplified HSV-2 ICP0 sequences covering 268 bp upstream of the HSV-2 ICP0 open reading frame (ORF) to 40 bp downstream of the poly A signal of ICP0 coding sequences. pHSV2.ICP0-V is an HSV-2 ICP0 cloning plasmid, derived from plasmid pHSV-2/ICP0, by replacing the Xho I-ICP0 DNA fragment containing sequences 25 bp upstream of the initiation codon of ICP0 to 397 bp upstream of the stop codon of ICP0 ORF with a Xho I-containing multiple cloning sequence (MCS). Plasmid pHSV2.ICP0-lacZ was created by inserting HindIII-Not I-LacZ gene-containing fragment of pcDNA3-lacZ into pHSV2.ICP0-V at the Hind III-Not I sites. pcmvtetO-UL9C535C is a plasmid encoding UL9-C535C under control of the tetO-containing hCMV immediate-early promoter (68). p02lacZ-TOC535C, expressing UL9-C535C driven by the tetO-containing hCMV major immediate-early promoter (FIG. 1A), was constructed by replacing the EcoR I/Age I-lacZ containing fragment of pHSV2.ICP0-lacZ with the EcoR I/Hind III-hcmvtetO-UL9C535C containing fragment of pcmvtetOUL9-C535C (69).

pAzgD-HSV-2 is an HSV-2 gD2-encoding plasmid kindly provided by Dr. Patricia Spear (Northwestern University). pICP4TO-hEGF expresses human epidermal growth factor under control of the tetO-bearing HSV-1 immediate-early ICP4 promoter, which consists of HSV-1 ICP4 promoter sequence from −377 bp to −19 bp relative to the transcriptional start site of ICP4 gene. Similar to the tetO-bearing hCMV major immediate-early promoter in plasmid pcm-vtctO-hEGF (73), the tetO-containing ICP4 promoter contains two tandem copies of tet operators at 10 bp downstream of the ICP4 TATA element, TATATGA. Thus, like pcmvtetO-hEGF, hEGF-expression from pICP4TO-hEGF can be tightly regulated by tetracycline in the presence of tetR, and insertion of the tetO has no effect on the ICP4 promoter activity in the absence of tetR. An additional unique feature associated with the tetO-bearing ICP4 promoter in pICP4TO-hEGF is the absence of the ICP4 DNA binding sequence ATCGTCCA-CACGGAG (SEQ ID NO:3), which spans the transcription initiation site of ICP4 gene (51) in the wild-type ICP4 promoter. Thus, unlike the wild-type ICP4 promoter that is subject to auto-regulation by ICP4 (16, 57), the tetO-bearing ICP4 promoter in pICP4TO-hEGF will not be suppressed by the HSV-1 major-regulatory protein ICP4.

To clone gD2 under the control of the tetO-containing ICP4 promoter, we first constructed plasmid p02ICP4-TO by cloning the Sma I-Bam HI tetO-containing ICP4 promoter in pICP4TO-hEGF into pHSV2.ICP0-V into the MCS of the vector. p02.4TO-gD2 is a p02ICP4-TO derived plasmid that encodes gD2 gene of pAzgD-HSV-2 under control of the tetO-bearing ICP4 promoter.

p02lacZTO-gD2.C535C, a plasmid encoding UL9-C535C under the control of the tetO-bearing hCMV immediate-early promoter with a 5' truncation at −236 bp of the hCMV promoter and the gD2 gene under control of the tetO-ICP4 promoter (FIG. 1A), was created by replacing the SnaB I/Pst I fragment of p02lacZTO-C535C with a Hind III/Pst I-gD2-containing fragment of p02.4TO-gD2. In p02lacZTO-gD2.C535C, the transcription of UL9-C535C gene and gD2 gene are in an opposite orientation.

Viruses

Wild-type HSV-2, strains 186 and G, were propagated and plaque-assayed on Vero cells. N2-lacZ is a HSV-2 ICP0 null mutant encoding the Lac Z gene under the control of HSV-2 ICP0 promoter, in which both copies of the ICP0 gene are replaced by the Lac Z gene in pHSV2.ICP0-lacZ through homologous recombination by transfecting U2OS cells with Nhe I-linearized pHSV2.ICP0-lacZ followed by HSV-2 superinfection as previously described (74). The replacement of the ICP0 gene with the Lac Z gene at the ICP0 locus was confirmed by PCR analysis of N2-lacZ viral DNA with the primers that flank the ICP0 gene and primers specific for the lac Z gene (41, 74).

Figure 1B:
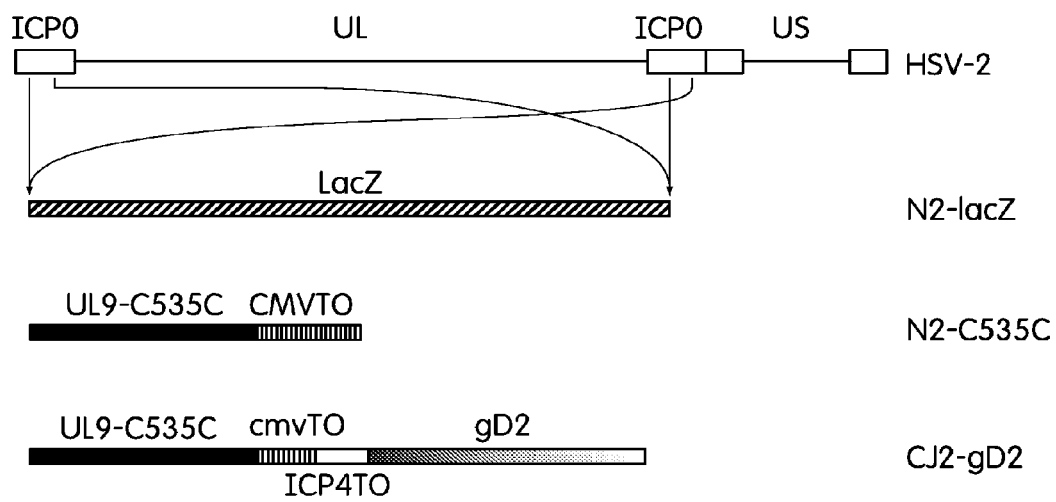

N2-C535C is a derivative of N2-lacZ, in which both copies of the Lac Z gene are replaced with DNA sequences encoding UL9-C535C under control of the tetO-containing hCMV promoter in plasmid p02lacZ-TOC535C (FIG. 1B). In brief, U2CEP4R11 cells were co-transfected with the linearized p02lacZ-TOC535C and infectious N2-lacZ viral DNA by Lipofectamine 2000. Progeny of the transfection were screened for the recombinational replacement of the lacZ genes of N2-lacZ with the DNA sequence containing the cmvtetOUL9-C535C by standard plaque assays. Plaques were stained with 5-bromo-4-chloro-3-indolyl-b-D-galactopyranoside (X-Gal) 96 hr postinfection. White plaques, reflecting the replacement of both copies of the lacZ gene by the UL 9-C535C DNA-encoding sequence, were isolated. One of the isolates, designated N2-C535C, yielded uniformly white plaques after four rounds of plaque purification.

CJ2-gD2 is constructed by replacing both copies of the Lac Z gene at the ICP0 locus in N2-lacZ with DNA sequences encoding UL9-C535C under the tetO-bearing hCMV major immediate-early promoter and gD2 under the control of the tetO-containing HSV-1 ICP4 promoter (FIG. 1B), which consists of HSV-1 ICP4 promoter sequence from −377 bp to −19 bp relative to the transcriptional start site of ICP4 gene (71).

SDS-PAGE and Western Blot Analysis

Vero cells seeded in 60 mm dishes at $7.5 \times 10^5$ cells/dish were mock-infected or infected with indicated viruses at an MOI of 10 PFU/cell. Cell extracts were prepared at 9 h or 16 h post-infection (72). Proteins in the cell extract were resolved by sodium dodecyl sulfate-polyacrylamide gel electrophoresis (SDS-PAGE) (9% acrylamide), transferred to polyvinylidene difluoride (PVDF) membranes, and probed with either polyclonal antibodies against HSV-1 gD (R45, a gift of Drs. Gary H. Cohen and Roselyn J Eisenberg), UL9 (a gift of Mark Challberg), or monoclonal antibodies specific for ICP27 and gB (Santa Cruz Biotechnology, Santa Cruz, Calif.).

Mice

Female BALB/c mice 4-6 weeks of age were purchased from Charles River Laboratories (Wilmington, Mass.). Mice were housed in metal cages at four mice per cage and maintained on a 12 h-light/dark cycle. Mice were allowed to acclimatize to the housing conditions for 1 week prior to experimentation. All animal experiments were conducted according to the protocols approved by Harvard Medical Area Standing Committee on Animals and the American Veterinary Medical Association.

Immunization and Challenges

BALB/c mice were randomly divided into several groups and the hair on their left rear flank was trimmed. Mice were either vaccinated with $2 \times 10^6$ PFU/mouse of CJ2-gD2, N2-C535C, CJ9-gD, or mock-vaccinated with DMEM in a volume of 30 µl s.c. in the left rear flank using a 1-ml syringe fitted with a 27-gauge needle. Mice were boosted after 2 weeks and challenged with wild-type HSV-2 strain G 3 weeks after secondary immunization. Five days prior to challenge, mice were injected s.c. in the neck ruff with medroxyprogesterone (SICOR Pharmaceuticals, Inc., Irvine, Calif.) at 3 mg per mouse in a volume of 20 µl (7, 50). For intravaginal challenge, mice in all groups were anesthetized, preswabbed with a calcium alginate swab (Sterile urethro-genital calcium alginate tipped applicator, Puritan Medical Products company LLC, Guilford, Me. USA) and inoculated intravaginally with 20 µl of culture medium containing $5 \times 10^5$ PFU (50 $LD_{50}$) of HSV-2 strain G (50). Animals were kept on their backs with their rear part elevated under the influence of anesthesia for 30-45 min post-infection.

Acute Infection Assays and Clinical Observations

On days 1, 2, 3, 5, and 7 post-challenge, vaginal mucosac were swabbed with calcium alginate (7). Infectious viruses in swab materials were assessed by standard plaque assay on Vero cell monolayers. Following challenge with wild-type HSV-2, mice were assessed daily during a 21-day follow-up period for signs of genital lesions and systemic illness. The severity of disease were scored as follows: 0=no sign of herpetic infection, 1=slight genital erythema and edema, 2=moderate genital inflammation, 3=purulent genital lesions and/or systemic illness, 4=hind-limb paralysis, and 5=death (8, 50).

Detection of HSV-2-Specific Neutralizing Antibodies

Blood was collected from tail veins of immunized and mock-immunized mice 4 weeks after primary immunization. Neutralizing serum antibody titers were determined as previously described in the presence of complement (5-7) with 250 PFU of wild-type HSV-2 strain 186. The neutralizing antibody titer was expressed as the final serum dilution required to achieve a 50% reduction in HSV PFU relative to the HSV PFU obtained in medium plus complement alone.

Immunoprecipitation

U2OS cells seeded at $7.5 \times 10^6$ cells per 100-mm dish were mock-transfected or transfected with 10 µg of p02.4TO-gD by lipofectamine 2000 at 24 h post-seeding. Cell extracts were prepared at 48 h post-transfection (72). Immunoprecipitations were performed by mixing 10 µl of pooled serum collected from mock-immunized and immunized mice with 70 µl of cell extracts prepared above. The gD/mouse IgG-specific complexes were precipitated with Protein A (Pierce Classic IP kit, Pierce Biotechnology, Rockford, Ill.), resolved on SDS-PAGE and probed with the rabbit anti-gD-specific polyclonal antibody, R45, following by reacting with HRP-conjugated goat-anti-rabbit IgG (Santa Cruz Biotechnology, Santa Cruz, Calif.).

IFN-γ ELISPOT Assays

Female BALB/c mice were sham-immunized with DMEM or immunized with CJ2-gD2 at a dose of $2\times10^6$ PFU/mouse twice at 2-weeks apart. At 5 to 10 weeks post second immunization, sham-immunized and CJ2-gD2-immunized mice were mock-challenged or challenged with wild-type HSV-2 strain 186 s.c. at a dose of $1\times10^4$ PFU/mouse. Splenocytes were isolated from individual groups of mice (n=3) on days 4 or 5 post-challenge. The $CD4^+$ and $CD8^+$ T cell ELISPOT assay was carried out as previously described (42). In brief, $CD4^+$ and $CD8^+$ T cells were isolated from splenocytes using Dynal mouse CD4- or CD8-negative isolation kits and seeded in quadruplicate in a 96-well filtration plate pre-coated with anti-mouse IFN-γ specific monoclonal antibody (AN18) at $7.5\times10^4$ or $1.5\times10^5$ cells/well. After incubation at 37° C. for 20 h, wells were washed, reacted with biotinylated IFN-γ specific monoclonal antibody (R4-6A2, Mabtech) at room temperature, and incubated with Streptavidin-Alkaline Phosphatase (Mabtech). The IFN-γ spot-forming cells were detected by addition of BCIP/NBT substrate. Spots were counted in a dissecting microscope and the number of IFN-γ spot-forming cells (SFC) was expressed as the mean±SEM per million $CD4^+$ or $CD8^+$ T cells.

Quantitative Real-Time PCR

The lower lumbar and sacral part of the spinal column including spinal cord and dorsal root ganglia were collected 16 days after boost immunization or 21 days after intravaginal challenge with $5\times10^5$ PFU of HSV-2 strain G from 9 or 10 mice that had been either immunized with CJ2-gD2 or CJ9-gD. The spinal column was cut into 4 pieces and each piece was kept separately in 0.5 ml of normal growth medium and stored at -80° C. for further processing. Total DNA was isolated from each dorsal root ganglion using the DNeasy tissue kit (Qiagen, Santa Clarita, Calif.), and suspended in 400 μl AE buffer. The presence of HSV-2 DNA was quantified by real-time PCR (Applied Biosystems 7300 Real-Time PCR System) with 100 ng of ganglia DNA and primers specific to the HSV DNA polymerase (Forward: 5' GCT CGA GTG CGA AAA AAC GTT C (SEQ ID NO:4), Reverse: 5' CGG GGC GCT CGG CTA AC (SEQ ID NO:5)) as previously described (8). The minimal copies of HSV-2 viral DNA that can be reliably detected were 1 copy per reaction.

Statistical Analysis

For statistical analysis un-paired Student's t-tests were performed. Results are considered to be statistically significant when the P value is less than 0.05.

II. Results

Construction of CJ2-gD2

As the first step in generating a gD2- and UL9-C535C-expressing dominant-negative and replication-defective HSV-2 recombinant virus, we constructed an HSV-2 ICP0 deletion mutant, N2-lacZ, in which both copies of ICP0 gene in HSV-2 strain 186 are replaced by the LacZ gene under the control of the HSV-2 ICP0 promoter (FIG. 1B). We show that, similar to the HSV-1 ICP0 null mutant 7314 (11), the plaque-forming efficiency of N2-lacZ on human osteosarcoma line U2OS cells is 425-fold higher than in Vero cells, indicating that the cellular activity in U2OS cells can also functionally substitute for HSV-2 ICP0. Compared with wild-type HSV-2, replication efficiency of N2-lacZ in Vero cells is reduced over 600-fold at an MOI of 0.1 PFU/cell. Consistent with this finding, intravaginal inoculation of N2-lacZ at $1\times10^5$ and $5\times10^5$ PFU/mouse led to no local or systemic illness, while mice infected with $1\times10^4$ PFU/mouse of wild-type HSV-2 developed severe genital herpes, and all died by day 11 post-infection. Moreover, N2-lacZ fails to establish reactivatable latent infection following intravaginal infection at a dose of $5\times10^5$ PFU/mouse. These results indicate that, similar to HSV-1 ICP0 (10, 11, 37, 64), deletion of HSV-2 ICP0 significantly impairs the ability of the virus to initiate acute and reactivatable latent infection in vivo.

Aiming to maximize levels of gD2 expression by a dominant-negative and replication-defective HSV-2 viral recombinant, we constructed a dominant-negative and replication-defective HSV-2 recombinant (CJ2-gD2) by replacing both copies of the Lac Z gene in N2-lacZ with DNA sequences encoding the gD2 gene driven by the tetO-bearing HSV-1 major immediate-early ICP4 promoter and UL9-C535C under control of the tetO-containing hCMV major immediate-early promoter with a truncation at the -236 bp of the full-length of hCMV immediate-early promoter (FIG. 1B). Thus, unlike CJ9-gD, which encodes a single copy of the inserted HSV-1 gD gene driven by the tetO-containing hCMV promoter at the HSV-1 UL9 locus (41), CJ2-gD2 contains 2 copies of gD2 gene controlled by the tetO-bearing HSV-1 immediate-early ICP4 promoter, which consists of HSV-1 ICP4 promoter sequence from -377 bp to -19 bp relative to the transcriptional start site of ICP4 gene. N2-C535C is an HSV-2 recombinant in which both copies of the Lac Z gene in N2-lacZ are replaced by UL9-C535C under the control of the full-length tetO-bearing hCMV immediate-early promoter.

CJ2-gD2 Expresses High Levels of gD2 and UL9-C535C in Infected Vero Cells

Figure 2A:
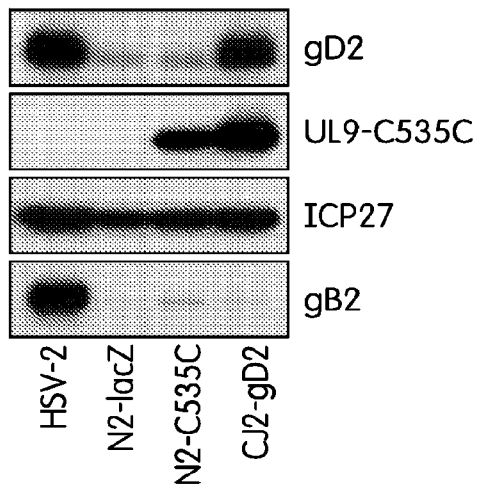
FIGS. 2A and 2B: These figures show high-level expression of gD2 and UL9-C535C following CJ2-gD2 infection of Vero cells.

To examine expression of gD2 and UL9-C535C from the tetO-bearing HSV-1 immediate-early ICP4 promoter and hCMV immediate-early promoter, respectively, Vero cells were infected with wild-type HSV-2, N2-lacZ, N2-C535C, and CJ2-gD2 at a MOI of 10 PFU/cell and harvested at 9 h post-infection. Infected cell proteins were analyzed by western blot assays with an HSV-1/2 ICP27 monoclonal antibody, a UL9 polyclonal antibody, and a gD1 polyclonal antibody (R45). Given that, like gD2, gB2 is the major target for neutralizing antibody as well as T-cell responses and is a γ1 product, infected cell proteins were also probed with a gB-specific monoclonal antibody. FIG. 2A shows that CJ2-gD2 and N2-C535C express similar levels of HSV-2 immediate-early protein ICP27 to those expressed by wild-type HSV-2 and N2-lacZ. While significant amounts of UL9-C535C were detected in CJ2-gD2- and N2-C535C-infected cells, little gD2 or gB2 was detected in N2-C535C-infected cells. In contrast to N2-C535C infection, however, infection of Vero cells with CJ2-gD2 leads to high-level expression of gD2 at levels similar to those in cells infected by wild-type HSV-2, and gD2 expression has no effect on gB2 expression. The results also indicate that, like the HSV-1 ICP0 null mutant 7134 (71), deletion of HSV-2 ICP0 in N2-lacZ greatly reduces gD2 expression. Due to the very low-level expression of UL9 from its authentic HSV early promoter (68), no wild-type UL9 was detected among cells infected by these four different viruses. Additionally, we observe that levels of UL9-C535C expressed in CJ2-gD2-infected cells are consistently higher than in cells infected by N2-C535C, suggesting that the HSV VP16 responsive elements, TAATGARAT, present in the HSV-1 ICP4 promoter (71) can lead to enhanced expression of UL9-C535C from the hCMV-immediate-early promoter of the described hybrid ICP4/hCMV promoter system.

Figure 2B:
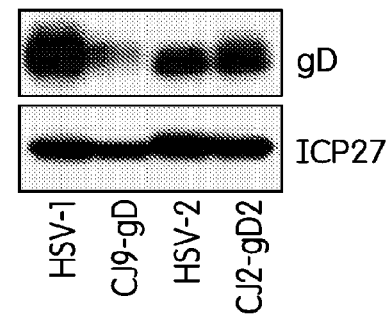

Western blot analysis with the gD1 polyclonal antibody (R45) presented in FIG. 2B shows that while much higher levels of gD were detected in wild-type HSV-1-infected cells than in cells infected with wild-type HSV-2, levels of gD detected in CJ9-gD-infected cells were markedly lower than in cells infected by CJ2-gD2. This finding demonstrates that CJ2-gD2 expresses gD2 more efficiently than gD1 expressed by CJ9-gD.

Figure 3:
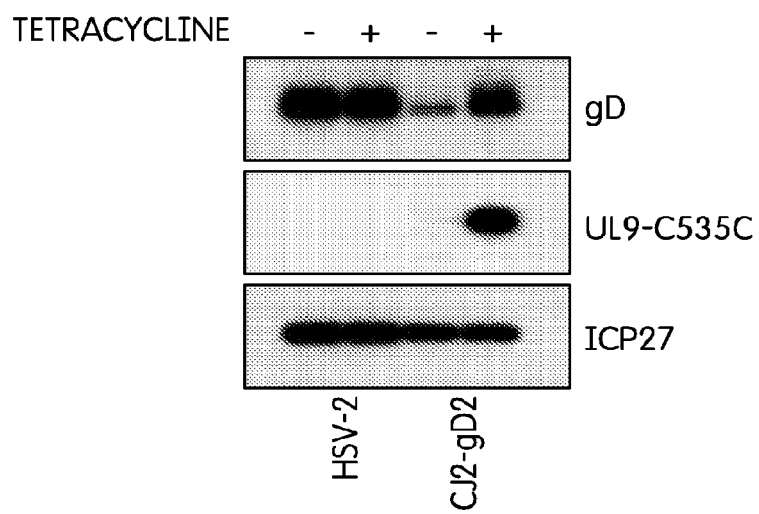
FIG. 3.

To demonstrate that the UL9-C535C and gD2 expressed in CJ2-gD2-infected Vero cells are indeed under the control of the tetO-bearing promoters, we next infected a stable tetR-expressing Vero cell line, VCEP4R-28 cells, with wild-type HSV-2 and CJ2-gD2 at an MOI of 10 PFU/cell in the absence or presence of tetracycline. Proteins from infected cells were harvested at 9 h post-infection and analyzed by western blots. As can be seen (FIG. 3), although similar levels of ICP27 were detected in wild-type HSV-2- and CJ2-gD2-infected VCEP4R-28 cells in both the absence and presence of tetracycline, UL9-C535C was detected in CJ2-gD2-infected VCEP4R-28 cells only when tetracycline was present and significantly higher levels of gD2 were detected in the presence of tetracycline than in its absence.

CJ2-gD2 Cannot Replicate in Vero Cells

Because of the lack of ICP0 and high-level expression of UL9-C535C from the tetO-bearing hCMV major immediate-early promoter, CJ2-gD2 had to be constructed and propagated in the tetR-expressing ICP0 complementing U2OS cell line U2CEP4R11 (68). We plaque-assayed $6.65 \times 10^7$ PFU of CJ2-gD2 on Vero cell monolayers and detected no infectious virus, demonstrating that the plaque-forming efficiency of CJ2-gD2 in Vero cells is reduced at least $6.65 \times 10^7$-fold compared with its complementing U2CEP4R11 cells.

Inhibition of Wild-type HSV-2 Replication by CJ2-gD2

Figures 4A, 4B:
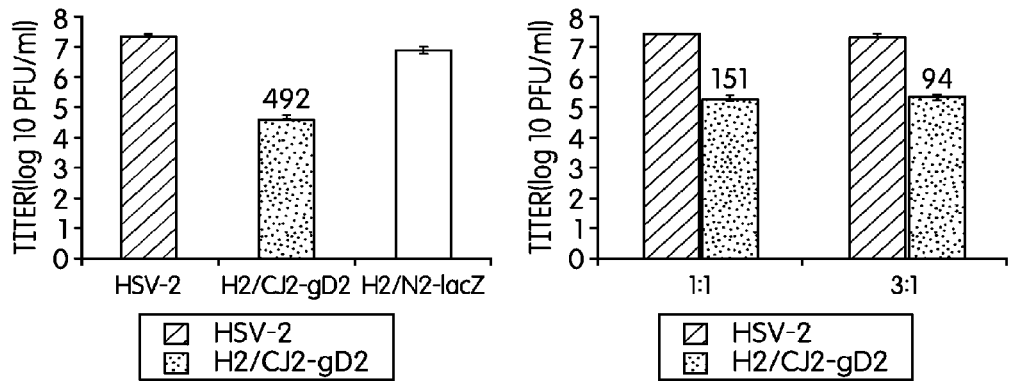
FIGS. 4A and 4B: These figures show the trans-dominant-negative effect of CJ2-gD2 on replication of wild-type HSV-2.
Figure 5A:
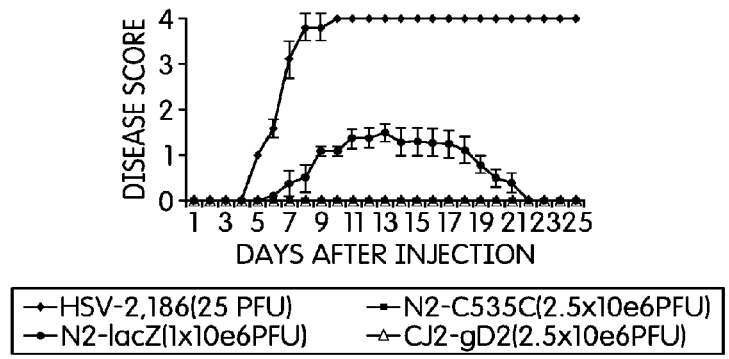
FIGS. 5A and 5B: These figures show the neurovirulence of wild-type HSV-2, strain 186, N2-lacZ, N2-C535C, and CJ2-gD2 in BALB/c mice following intracerebral inoculation. Female BALB/c mice 4 to 6-weeks-old were randomly assigned to five groups of 8 mice each. Mice were anesthetized with sodium pentobarbital and inoculated with either DMEM, 25 PFU/mouse of wild-type HSV-2 strain 186, $1 \times 10^6$ PFU/mouse of N2-lacZ, $2.5 \times 10^6$ PFU/mouse of CJ2-gD2 or N2-C535C through intracerebral injection into the left frontal lobe of the brain in a volume of 20 µl at a depth of 4 mm. Mice were examined for signs and symptoms of illness for 35 days after inoculation.
Figure 5B:
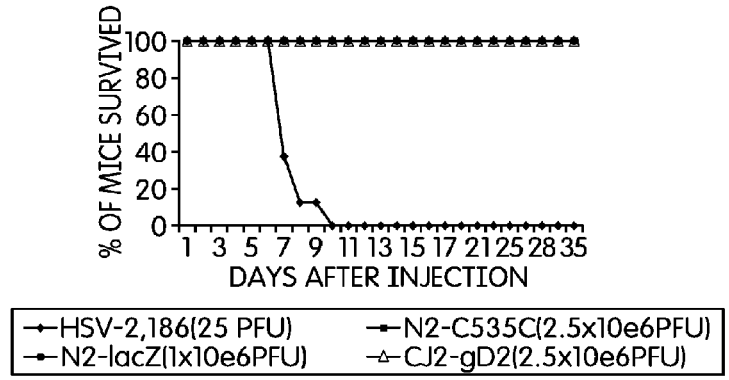
Figure 6A:
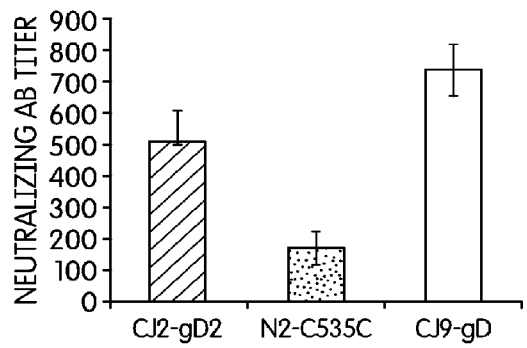
FIGS. 6A and 6B.
Figure 6B:
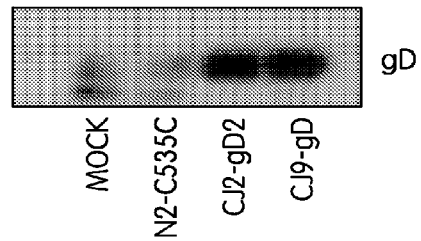
Figure 7A:
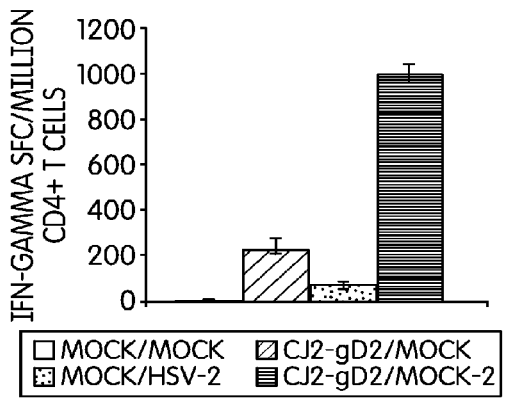
FIGS. 7A-7D: These figures are concerned with the induction of HSV-2-specific CD4+ and CD8+ T-cell responses in CJ2-gD2-immunized mice. Female BALB/c mice were either sham-immunized or immunized with CJ2-gD2 at $2 \times 10^6$ PFU per mouse twice at 2-week interval.
Figure 7B:
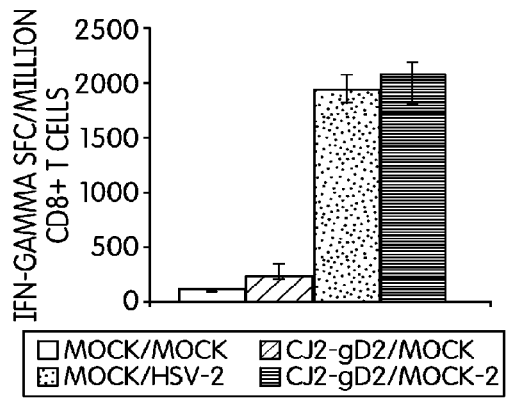
Figure 7C:
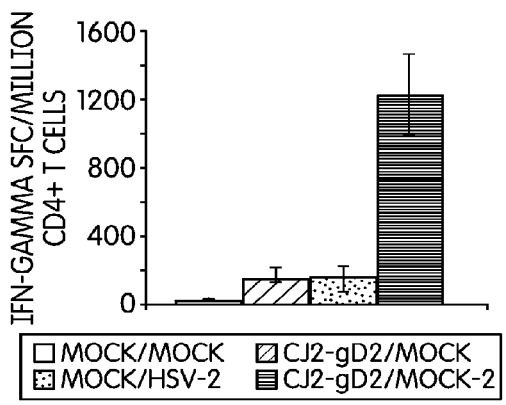
Figure 7D:
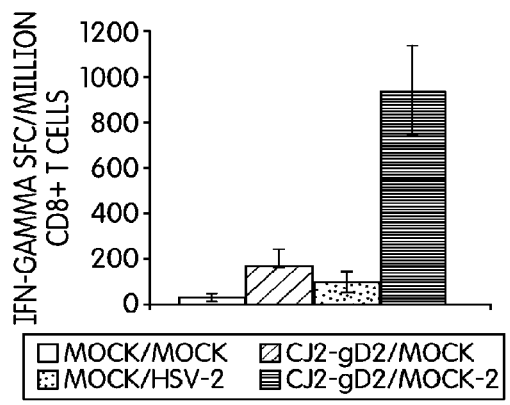

We next tested the dominant-negative effect of high-level UL9-C535C expression by CJ2-gD2 on the replication of wild-type HSV-2 viral replication by the co-infection assay (FIG. 4). FIG. 4A shows that co-infection of Vero cells with CJ2-gD2 at a MOI of 5 PFU/cell and wild-type HSV-2 at an MOI of 2 PFU/cells led to a nearly 500-fold decrease in wild-type HSV-2 production compared with cells singly infected by wild-type HSV-2 at the same MOI, regardless of whether the virus titers were determined in Vero cells or in U2CEP4R11 cells. Little reduction in wild-type virus yield was detected when a similar co-infection experiment was performed with N2-lacZ.

To further examine the potency of CJ2-gD2 in inhibiting the replication of wild-type HSV-2, we carried out co-infection experiments with wild-type HSV-2 and CJ2-gD2 at MOI ratios of 1:1 and 3:1, respectively. The results in FIG. 4B show that CJ2-gD2 is effective in preventing wild-type HSV-2 infection under both conditions, leading to about 151- and 94-fold reduction in wild-type virus synthesis at the indicated co-infection ratios compared with cells singly infected with the wild-type HSV-2 at MOIs of 5 PFU/cell and 15 PFU/cell, respectively.

CJ2-gD2 is Avirulent Following Intracerebral Injection in Mice

Neurovirulence is one of the hallmarks of HSV infection. To determine the ability of CJ2-gD2 and N2-C535C to replicate in the CNS, female BALB/c mice 5 to 6-weeks-old were randomly assigned to five groups of 8 mice each. CJ2-gD2 and N2-C535C were directly inoculated into the brain of each mouse at the left frontal lobe at $2.5\times10^6$ PFU per mouse in a 20 μl volume with a 28-gauge insulin needle at the depth of 4 mm (74). Morbidity and mortality were monitored for 35 days. Given that the $LD_{50}$ of wild-type HSV-2 strain 186 is around 10 PFU in female BALB/c mice after intravitreal injection (38), a group of mice were also inoculated with wild-type HSV-2 at 25 PFU/mouse. As an additional control, mice in the fifth group were inoculated with N2-lacZ at $1\times10^6$ PFU/mouse. FIG. 5 shows that, like mice inoculated with DMEM, mice intracerebrally inoculated with CJ2-gD2 and N2-C535C at a dose of $2.5\times10^6$ PFU showed no signs of neurovirulence during a 35-day follow-up, while all mice inoculated with wild-type HSV-2 at a dose of 25 PFU/mouse (a 100,000-fold lower dose than that given to mice inoculated with CJ2-gD2) died by day 10 post-inoculation, and all inoculated mice exhibited signs of CNS illness commonly associated with HSV-2 infection, including roughened fur, hunched posture, ataxia, and anorexia. Although 100% of mice inoculated with N2-lacZ survived, all mice exhibited signs of encephalitis.

Induction of HSV-2-Specific Neutralizing Antibodies and a gD2-Specific

Antibody Response in Mice Immunized with CJ2-gD2

The ability of CJ2-gD2 to elicit anti-HSV-2-specific neutralizing antibodies was determined in mice immunized with CJ2-gD2 at a dose of $2\times10^6$ PFU. As controls, groups of mice were also immunized with N2-C535C or CJ9-gD at the same dose. As shown (FIG. 6A), the average of the HSV-2-specific neutralization antibody titer in mice immunized with CJ2-gD2 were on average 500, which is 3-fold higher than that of mice immunized with N2-C535C ($p=0.015$), and is comparable to the neutralizing antibody titer induced in CJ9-gD immunized mice ($p=0.28$). No specific antibody titers against HSV-2 were detected in mock-vaccinated mice at a 1:10 dilution.

FIG. 6B shows that while similar levels of gD-specific antibody response were detected between mice immunized with CJ2-gD2 and CJ9-gD when the respective immunoprecipitated gD2 complexes were probed with anti-gD1 antibodies, R45, levels of anti-gD-specific antibodies in mice immunized with CJ2-gD2 were significantly higher than in mice immunized with N2-C535C and mock-immunized control. Taken together, the results presented in FIG. 6 indicate that high-level expression of gD2 bp CJ2-gD2 leads to increased efficacy in eliciting anti-gD2 antibody as well as anti-HSV-2-specific neutralizing antibody responses compared with N2-C535C.

Induction of HSV-2-Specific T-Cell Response in Mice Immunized with CJ2-gD2

To evaluate the effectiveness of CJ2-gD2 immunization in eliciting HSV-2-specific T-cell response, we carried out the recall experiment to examine the memory T-cell responses in immunized mice following challenge with wild-type HSV-2. First, sham-vaccinated and CJ2-gD2-vaccinated mice were either mock-challenged or challenged with wild-type HSV-2 at 9-10 weeks post-boost immunization followed by IFN-γ ELISPOT assays with $CD4^+$ and $CD8^+$ T cells isolated from spleens of individual groups of mice (n=3) on day 5 post-challenge (FIG. 7A). CJ2-gD2-vaccinated mice challenged with wild-type HSV-2 had a 4.8-fold increase of IFN-γ-positive $CD4^+$ T cells compared with the mock-infected CJ2-gD2-immune mice ($p<0.0001$). More significantly, the number of IFN-γ-secreting $CD4^+$ T cells detected in HSV-2-infected mice previously vaccinated with CJ2-gD2 was 18-fold more than HSV-2-infected sham-vaccinated mice ($p<0.0001$). No IFN-γ-positive $CD4^+$ T cells were detected in sham-vaccinated mock-infected control mice under identical conditions. These findings show that immunization with CJ2-gD2 elicits strong memory $CD4^+$ T cell response.

While there was a greater than 2-fold increase in IFN-γ-secreting $CD8^+$ T cells in CJ2-gD2-vaccinated mice compared with the sham-vaccinated controls, similar numbers of IFN-γ-secreting CD8⁺ T cells were detected in the spleens of HSV-2-infected sham-vaccinated mice and HSV-2-infected CJ2-gD2-vaccinated mice (FIG. 7B). We thus carried out the second set of recall experiments, in which sham-vaccinated and CJ2-gD2-vaccinated mice were either mock-challenged or challenged with wild-type HSV-2 (n=3) 5-6 weeks post-second vaccination. CD4⁺ and CD8⁺ ELISPOT assays were performed on day 4 post-infection (FIGS. 7C and 7D). An 8.6- and 5.7-fold increase in IFN-γ-secreting CD4⁺ and CD8⁺ T cells, respectively, was detected in CJ2-gD2 immune mice following HSV-2 infection compared with mock-infected CJ2-gD2 immune mice (CD4 T cells: $p=0.035$; CD8⁺ T cells: $p=0.01$). Moreover, following challenge with HSV-2, IFN-γ-secreting CD4⁺ and CD8⁺ T cells were 8- and 9.5-fold higher, respectively, in CJ2-gD2 vaccinated compared with sham-vaccinated mice (CD4⁺ T cells: $p=0.036$; CD8⁺ T cells: $p=0.01$). Collectively, these studies demonstrate that immunization with CJ2-gD2 can elicit robust HSV-2-specific memory CD4⁺ and CD8⁺ T-cell responses, which can be efficiently recalled during HSV-2 infection.

Protection Against HSV-2 Genital Infection and Disease in Immunized Mice

Figure 8:
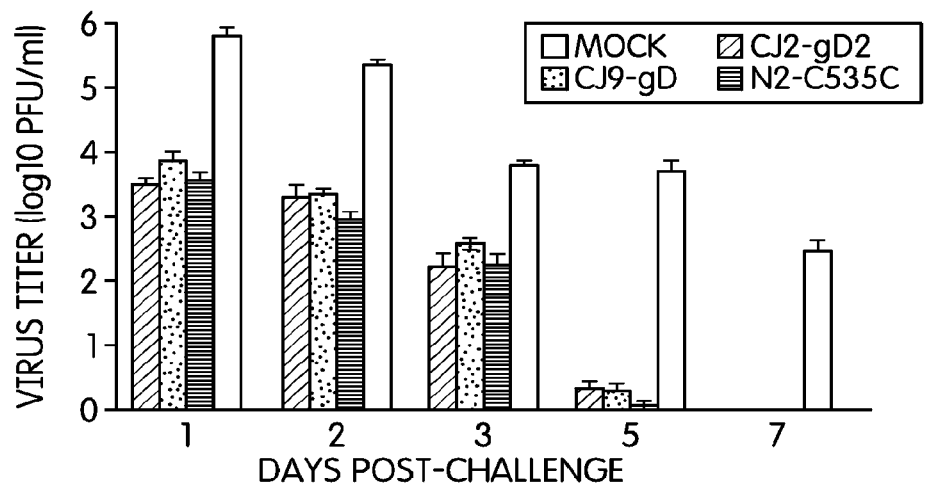
FIG. 8.

Five to six weeks after the initial immunization, mice were challenged intravaginally with HSV-2 strain G at 50 LD$_{50}$ (5×10⁵ PFU/mouse). Vaginal swabs were taken on days 1, 2, 3, 5, and 7 after challenge. Mice were observed during a 21-day follow-up period for the incidence of genital and disseminated HSV-2 disease. As shown in FIG. 8A, yields of challenge virus were reduced more than 200-fold on day 1 ($p<0.001$) and 130-fold on day 2 ($p<0.0001$) in mice immunized with CJ2-gD2 (n=9) compared with those of mock-immunized control (n=10). Although there was no significant difference in reduction of challenge virus shedding on days 1, 2, and 3 post-challenge between groups of mice immunized with CJ2-gD2 and N2-C535C (n=10), immunization with CJ2-gD2 was more effective than CJ9-gD in reducing challenge virus shedding on days 1 ($p=0.03$), 2 ($p=0.025$), and 3 ($p<0.007$). Little or no challenge virus was detected in mice immunized with CJ2-gD2, N2-C535C, or CJ9-gD on day 5 post-challenge, whereas all mock-vaccinated mice continued to shed virus at an average yield of more than 5×10³ PFU/ml. No challenge virus was present in the vaginal swab materials collected on day 7 post-challenge in three immunized groups of mice. In a separate experiment, we observed that while there was no virus shedding in CJ2-gD2-immunized mice on day 5 post-challenge, presence of wild-type HSV-2 was detected in 5 out of 7 N2-C535C-immunized mice and 4 out of 7 CJ9-gD-immunized mice.

Figure 9A:
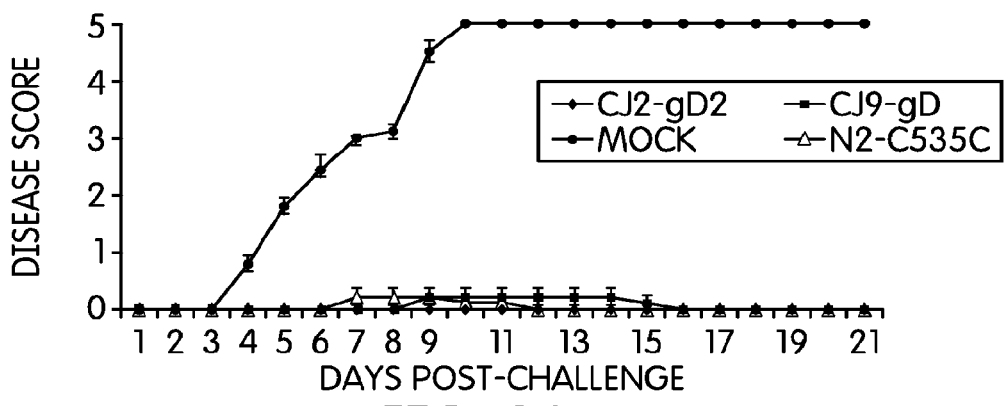
FIGS. 9A and 9B: These figures show the prevention of HSV-2 disease in mice immunized with CJ2-gD2. After challenge with wild-type HSV-2, individual mice described in the legend of FIG. 8 were observed during a 21-day follow-up period for the incidence of genital and disseminated HSV-2 disease (FIG. 9A) and survival (FIG. 9B) using the following scale: 0=no sign, 1=slight genital erythema and edema, 2=moderate genital inflammation, 3=purulent genital lesions and/or systemic illness, 4=hind-limb paralysis, 5=death.
Figure 9B:
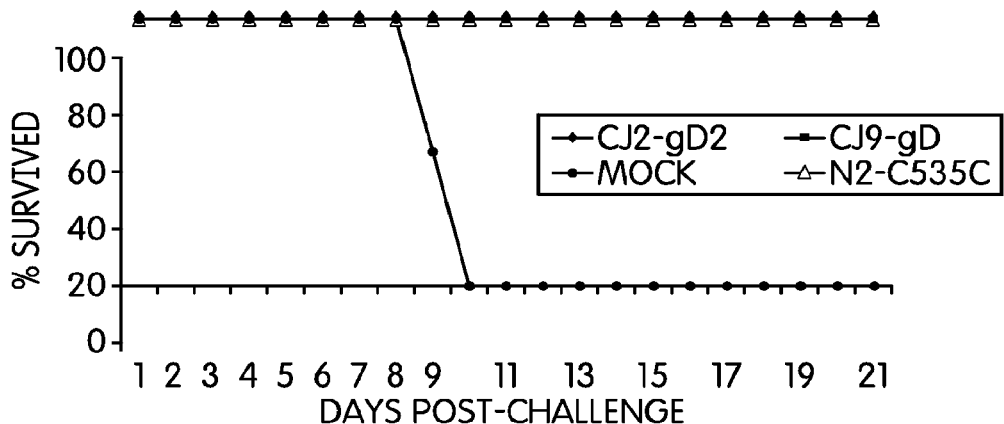

The results in FIG. 9 show that mice immunized with CJ2-gD2 were completely protected from development of local genital lesions and exhibited no signs of systemic disease after challenge with wild-type HSV-2 (FIG. 9A). All mock-immunized mice developed severe genital lesions and succumbed to the wild-type HSV-2 infection by day 11 post-challenge (FIG. 9B). Although immunization with N2-C535C and CJ9-gD protected mice against lethal challenge with wild-type HSV-2, 20% and 30% of mice experienced a transient low degree of local genital disease (score 1) in N2-C535C- and CJ9-gD-immunized mice, respectively (Table 1). In a similar experiment (Table 1), it was observed that among mice immunized with CJ9-gD (n=7), 2 mice experienced low degrees of local genital disease, and 1 mouse showed sign of systemic illness and died on day 14 post-challenge, and 3 out of 7 N2-C535C-immunized mice (43%) showed a low degree of local genital disease (score=1). Again, no signs of local and systemic herpetic disease were seen in CJ2-gD2-immunized mice (n=7). Collectively, these studies demonstrate that CJ2-gD2 is a more effective vaccine than N2-C535C and CJ9-gD in protection mice against genital disease following intravaginal challenge with wild-type HSV-2.

TABLE 1

Percentage of protection against herpetic disease in mock-immunized and immunized mice following intravaginal challenge with wild-type HSV-2

| | Mock | CJ2-gD2 | N2-C535C | CJ9-gD |
|---|---|---|---|---|
| Exp 1 (n = 9-10) | 0 | 100% | 80% | 70% |
| Exp 2 (n = 7-8) | 0 | 100% | 57% | 57% |

REFERENCES

1. Abu-Raddad, et al., *PLoS ONE* 3:e2230 (2008).
2. Ackermann, et al., *J. Virol.* 52:108-18 (1984).
3. Adelson, et al., *J. Clin. Virol.* 33:25-34 (2005).
4. Arvin, et al., *Infect. Immun.* 40:184-9 (1983).
5. Augustinova, et al., *J. Virol.* 78:5756-65 (2004).
6. Bourne, et al., *Vaccine* 14:1230-4 (1996).
7. Brans, et al., *J. Invest. Dermatol.* 129:2470-9 (2009).
8. Brans, et al., *J. Invest. Dermatol.* 128:2825-32 (2008).
9. Bryson, et al., *J. Infect. Dis.* 167:942-6 (1993).
10. Cai, et al., *J. Virol.* 67:7501-12 (1993).
11. Cai, et al., *J. Virol.* 63:4579-89 (1989).
12. Cohen, et al., *J. Virol.* 49:102-8 (1984).
13. Coleman, et al., *J. Clin. Microbiol.* 18:287-91 (1983).
14. Cooper, et al., *Cell. Immunol.* 239:113-20 (2006).
15. Corey, et al., *N. Engl. J. Med.* 314:749-57 (1986).
16. DeLuca, et al., *J. Virol.* 62:732-43 (1988).
17. Dolan, et al., *J. Virol.* 72:2010-21 (1998).
18. Dudek, et al., *Virology* 344:230-9 (2006).
19. Fleming, et al., *N. Engl. J. Med.* 337:1105-11 (1997).
20. Freeman, et al, *Aids* 20:73-83 (2006).
21. Glorioso, et al., *J. Virol.* 50:805-12 (1984).
22. Grammer, et al., *J. Immunol.* 145:2249-53 (1990).
23. Gupta, et al., *Lancet* 370:2127-37 (2007).
24. Handler, et *Virol.* 70:6067-70 (1996).
25. Hirsch, Herpes simplex virus, p. 1144-1153. In G. L. Mandell, R. G. J. Douglas, and J. E. Bennett (ed.), Principles and practice of infectious diseases. Churchill Livingstone Inc., New York (1990).
26. Honess, et al., *J. Gen. Virol.* 22:159-69 (1974).
27. Hosken, et al., *J. Virol.* 80:5509-15 (2006).
28. Johnson, et al., *J. Immunol.* 145:702-10 (1990).
29. Jones, et al., *Herpes* 11:12-7 (2004).
30. Kim, et al., *J. Immunol.* 181:6604-15 (2008).
31. Koelle, et al., *Annu. Rev. Med.* 59:381-395 (2008).
32. Koelle, et al., *Clin. Microbiol. Rev.* 16:96-113 (2003).
33. Koelle, et al., *Curr. Eye Res.* 30:929-42 (2005).
34. Koelle, et al., *J. Clin. Invest.* 91:961-8 (1993).
35. Kousoulas, et al., *Virology* 166:423-31 (1988).
36. Lakeman, et al., *Sex. Transm. Dis.* 13:61-6 (1986).
37. Leib, et al., *J. Virol.* 63:759-68 (1989).
38. Lewandowski, et al., *J. Neuroimmunol.* 81:66-75 (1998).
39. Liesegang, *Cornea* 20:1-13 (2001).
40. Looker, et al., *Sex. Transm. Infect.* 81:103-7 (2005).
41. Lu, et al., *J. Invest. Dermatol.* 129:1174-84 (2009).
42. McGeoch, et al., *J. Gen. Virol.* 69:1531-74 (1988).
43. McGeoch et al., *J. Gen. Virol.* 72:3057-3075 (1991);
44. McGeoch et al., *Nucl. Acid Res.* 14:1727-1745 (1986)
45. McGeoch, et al., Nucleic Acids Res 14:3435-48 (1986).
46. Mertz, et al., *Ann. Intern. Med.* 116:197-202 (1992).

47. Mikloska, et al., *J. Gen. Virol.* 79:353-61 (1998).
48. Mikloska, et al., *J. Immunol.* 164:5167-76 (2000).
49. Minson, et al., *J. Gen. Virol.* 67 (Pt 6):1001-13 (1986).
50. Morrison, et al., *Virology* 243:178-87 (1998).
51. Muller, *J. Virol.* 61:858-65 (1987).
52. Nagot, et al., *N. Engl J. Med.* 356:790-9 (2007).
53. Para, et al., *J. Virol.* 55:483-8 (1985).
54. Pereira, *Dev. Biol. Stand.* 52:115-31 (1982).
55. Pereira, et al., *Infect. Immun.* 29:724-32 (1980).
56. Perry, et al., *J. Gen. Virol.* 67:2365-2380 (1986)
57. Roberts, et al., *J. Virol.* 62:4307-20 (1988).
58. Roizman, et al., Herpes simplex viruses and their replication, p. 2399-2459. In a. P. M. H. D. M. Knipe (ed.), Fields Virology, 4rd ed. Lippincott Williams & Wilkins, Philadelphia, Pa. (2001).
59. Schmidt, et al., *J. Infect. Dis.* 149:645-6 (1984).
60. Stanberry, *Herpes* 11 (*Suppl* 3):161A-169A (2004).
61. Stanberry, et al., *Clin. Infect. Dis.* 30:549-66 (2000).
62. Stanberry, et al., *N. Engl. J. Med.* 347:1652-61 (2002).
63. Starr, et al., *Gene Ther* 3:615-23 (1996).
64. Stow, et al., *J. Gen. Virol.* 67:2571-85 (1986).
65. Tigges, et al., *J. Virol.* 66:1622-34 (1992).
66. Whitley, et al., *Clin Infect Dis* 26:541-53; quiz 554-5 (1998).
67. Xu, et al., *J. Infect. Dis.* 185:1019-24 (2002).
68. Yao, et al., *Hum. Gene Ther.* 10:1811-8 (1999).
69. Yao, et al., *Hum. Gene Ther.* 10:419-27 (1999).
70. Yao, et al., *Antiviral Res.* 53:127-33 (2002).
71. Yao, et al., *J. Virol.* 69:6249-58 (1995).
72. Yao, et al., *J. Virol.* 68:8158-68 (1994).
73. Yao, et al., *Hum. Gene Ther.* 9:1939-50 (1998).
74. Yao, et al., *Mol. Ther.* 13:1133-41 (2006).
75. Zarling, et al., *J. Immunol.* 136:4669-73 (1986).

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A replication-defective, dominant-negative Herpes simplex virus 2 (HSV-2) recombinant virus, comprising within its genome:
   a) a first sequence encoding a first HSV-2 glycoprotein D (gD2) wherein said sequence is operably linked to a first promoter and said first promoter is operably linked to a first tetracycline operator (tet-O) sequence, wherein said first sequence encoding gD2 is inserted into a first ICP0 protein open reading frame;

b) a second sequence encoding a second HSV-2 gD2 wherein said second sequence is operably linked to a second promoter and said second promoter is operably linked to a second tet-O sequence, wherein said second sequence encoding gD2 is inserted into a second ICP0 protein open reading frame;

c) a third sequence encoding a first dominant negative mutant form of HSV-1 UL9 protein, wherein said third sequence is operably linked to a third promoter and said third promoter is operably linked to a third tetracycline operator (tet-O) sequence; and d) a fourth sequence encoding a second dominant negative mutant form of HSV-1 UL9 protein, wherein said fourth sequence is operably linked to a fourth promoter and said fourth promoter is operably linked to a fourth tetracycline operator (tet-O) sequence, wherein:

i) said first and said second promoters are HSV-1 or HSV-2 immediate early promoters;

ii) said third and said fourth promoters are induced in response to VP16; and iii) said recombinant virus does not comprise a sequence encoding a functional ICP0 protein.

2. The recombinant virus of claim 1, wherein at least one HSV-1 or HSV-2 immediate early promoter is an ICP4 promoter.

3. The recombinant virus of claim 2, wherein at least one ICP4 promoter has been modified to eliminate a functional ICP4 DNA binding sequence.

4. The recombinant virus of claim 1, wherein said first and/or said second mutant form of UL9 protein is UL9-C535C encoded by SEQ ID NO:2.

5. The recombinant virus of claim 4, wherein one or both of said first and said second promoters are ICP4 promoters.

6. The recombinant virus of claim 5, wherein at least one ICP4 promoter has been modified to eliminate a functional ICP4 DNA binding sequence.

7. The recombinant virus of claim 1, wherein said first and said second mutant form of UL9 protein is UL9-C535C encoded by SEQ ID NO:2.

8. The recombinant virus of claim 7, wherein one or both of said first and said second promoters are ICP4 promoters.

9. The recombinant virus of claim 8, wherein both said first and said second promoters are ICP4 promoters that have been modified to eliminate a functional ICP4 DNA binding sequence.

10. The recombinant virus of claim 1, wherein said third and/or said fourth promoter is a human cytomegalovirus (hCMV) immediate early promoter.

11. The recombinant virus of claim 10, wherein:

a) at least one of said first and said second promoters is an ICP4 promoter that has been modified to eliminate a functional ICP4 DNA binding sequence;

b) at least one of said third or said fourth promoters is an hCMV immediate early promoter that has been truncated and joined to the modified ICP4 promoter so as to form a hybrid promoter in which the hCMV immediate early promoter and the modified ICP4 promoter are in opposite orientation and wherein the hCMV immediate early promoter is positioned in said hybrid promoter so as to make it responsive to VP16.

12. The recombinant virus of claim 11, wherein said first and/or said second mutant form of UL9 protein is UL9-C535C encoded by a sequence shown in SEQ ID NO:2.

13. The recombinant virus of claim 11 or 12, wherein said recombinant virus also expresses one or more recombinant immunomodulating genes.

14. The recombinant virus of claim 1, wherein:

a) both said first and said second promoters are ICP4 promoters;

b) said third and/or said fourth promoter is an hCMV immediate early promoter that has been truncated and joined to said first and/or said second ICP4 promoter so as to form a hybrid in which hCMV and ICP4 promoters are in opposite orientation; and c) both said first and said second mutant form of UL9 protein is UL9-C535C encoded by SEQ ID NO:2.

15. The recombinant virus of claim 14, wherein at least one ICP4 promoter has been modified to eliminate a functional ICP4 DNA binding sequence.

16. The recombinant virus of claim 1, wherein said recombinant virus also expresses one or more recombinant immunomodulating genes.

17. The recombinant virus of claim 1, wherein said recombinant virus expresses IL15.

18. The recombinant virus of claim 1, wherein said recombinant virus also expresses HSV-2 glycoprotein B (gB) or HSV-2 glycoprotein C (gC) under the control of a tet-O bearing HSV or hCMV immediate-early promoter.

19. The recombinant virus of claim 18, wherein said recombinant virus expresses HSV-2 gB under the control of a tet-O bearing HSV or hCMV immediate-early promoter.

20. A replication-defective, dominant-negative Herpes simplex virus 2 (HSV-2) recombinant virus, comprising within its genome:
   a) a first sequence encoding a first HSV-2 glycoprotein D (gD2), wherein said first sequence is operably linked to a first ICP4 promoter that has been modified to eliminate a functional ICP4 DNA binding sequence, and wherein said first ICP4 promoter is operably linked to a first tetracycline operator (tet-O) sequence, wherein said first sequence encoding gD2 is inserted into a first ICP0 protein open reading frame;
   b) a second sequence encoding a second HSV-2 gD2, wherein said second sequence is operably linked to a second ICP4 promoter that has been modified to eliminate a functional ICP4 DNA binding sequence, and wherein said second ICP4 promoter is operably linked to a second tet-O sequence, wherein said second sequence encoding gD2 is inserted into a second ICP0 protein open reading frame;
   c) a third sequence encoding a first dominant negative mutant form of HSV-1 UL9 protein, wherein said third sequence is operably linked to a third promoter and said third promoter is operably linked to a third tetracycline operator (tet-O) sequence; and
   d) a fourth sequence encoding a second dominant negative mutant form of HSV-1 UL9 protein, wherein said fourth sequence is operably linked to a fourth promoter and said fourth promoter is operably linked to a fourth tetracycline operator (tet-O) sequence, wherein:
      i) said third and said fourth promoters are induced in response to VP16; and
      ii) said recombinant virus does not comprise a sequence encoding a functional ICP0 protein.

21. An immunogenic composition comprising the recombinant virus of claim 1 in unit dose form.

22. The immunogenic composition of claim 21, wherein said recombinant virus is present at a minimum of $1\times10^7$ plaque forming units (pfu) per unit dose.

23. A method of therapeutically reducing the symptoms in a patient with an HSV-1 or HSV-2 infection, comprising administering to said patient the immunogenic composition of claim 21.

24. The method of claim 23, wherein said patient is seropositive for either HSV-1 or HSV-2.

25. A method of eliciting an immune response in a patient against HSV-1 or HSV-2, comprising administering to said patient the immunogenic composition of claim 21.

26. The method of claim 25, wherein said patient is seropositive for either HSV-1 or HSV-2.

* * * * *